(12) United States Patent
Aguera et al.

(10) Patent No.: US 7,183,400 B1
(45) Date of Patent: Feb. 27, 2007

(54) USE OF ULIP PROTEINS IN THE DIAGNOSIS AND THERAPY OF CANCERS AND PARANEOPLASTIC NEUROLOGICAL SYNDROMES

(75) Inventors: Michèle Aguera, Caluire (FR); Marie-Françoise Belin, Lyons (FR); Jérôme Honnorat, Bron (FR); Pappachan Kolattukudy, Colombus, OH (US); ThanhTam Quach, Lyons (FR); Tamara Byk, Creteil (FR); André Sobel, Paris (FR); Dominique Aunis, Strasbourg (FR); Jean-Christophe Antoine, Chalin le Comtal (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 09/367,496

(22) PCT Filed: Feb. 19, 1998

(86) PCT No.: PCT/FR98/00328

§ 371 (c)(1),
(2), (4) Date: Nov. 24, 1999

(87) PCT Pub. No.: WO98/37192

PCT Pub. Date: Aug. 27, 1998

(30) Foreign Application Priority Data

Feb. 19, 1997 (FR) .................................. 97 01961

(51) Int. Cl.
*C07H 21/04* (2006.01)
(52) U.S. Cl. .................. 536/23.5; 435/320.1; 435/325; 530/350
(58) Field of Classification Search ............... 536/23.5; 435/320.1, 325, 7.1, 277.1; 530/350
See application file for complete search history.

(56) References Cited

U.S. PATENT DOCUMENTS 5,770,381 A * 6/1998 MacKay et al. ............. 435/7.1
6,066,475 A * 5/2000 Maclaren et al. .......... 435/69.3
6,455,267 B1 * 9/2002 Tobin et al. ................ 435/7.24

OTHER PUBLICATIONS

Hamajima, N, et al, Nov. 21, 1996, A novel gene family defined by human dihydropyrimidinase and three related proteins with differential tissue distribution, Gene, vol. 180, No. 1-2, pp. 157-163.*
Honnorat, J, et al, 1996, Antibodies to a subpopulation of glial cells and a 66 kDa developmental protein in patients with paraneoplastic neurological syndromes, Journal of Neurology, Neurosurgery, and Psychiatry, vol. 61, No. 3, pp. 270-278.*
Antoine, JC, et al, 1993, Posterior uveitis, paraneoplastic encephalomyelitis and auto-antibodies reacting with developmental protein of brain and retina, Journal of Neurological Sciences, vol. 117, pp. 215-223.*
Database GenBank Accession No. Y10976, Direct Submission (Byk, T, et al, Feb. 3, 1997), H. sapiens mRNA for Ulip4 protein.*
Gura, T, 1997, Systems for identifying drugs are often faulty, Science, vol. 278, pp. 1041-1042.*
Bodey, B, et al, 2000, Failure of cancer vaccines: the significant limitations of this approach to immunotherapy, Anticancer Research, vol. 20, pp. 2665-2676.*
Ezzell, C, 1995, Cancer "vaccines": an idea whose time has come?, Journal of NIH Research, vol. 7, pp. 46-49.*
Bergers, G, et al, 2000, Extrinsic regulators of epithelial tumor progression: metalloproteinases, Current Opinion in Genetics & Development, vol. 10, pp. 120-127.*
Splitler, LE, 1995, Cancer vaccines: the interferon analogy, Cancer Biotherapy, vol. 10, No. 1, pp. 1-3.*
Tockman, MS, et al, 1992, Considerations in bringing a cancer biomarker to clinical application, Cancer Research, vol. 52, Suppl., pp. 2711s-2718s.*
Database GenBank Accession No. AB006713, Hamajima N, Aug. 23, 1997 (see USPTO search report US-09-367-496-8.std.rge, pp. 1 and 2).*
Okajima T, et al. J Biochem (Tokyo) May 1995; 117 (5):980-6.*
Stefano JE. Cell Jan. 1984; 36 (1): 145-54.*
Holmes EH. Exp Opin Invest Drugs 2001; 10 (3): 511-9.*
Antoine JC, et al. J Neurol Neurosurg Psychiatry. Jul. 1999; 67 (1): 7-14.*
Greenspan NS, et al. Nat Biotechnol. Oct. 1999; 17 (10): 936-7.*
Burgess WH, et al. J Cell Biol. Nov. 1990; 111(5 Pt 1):2129-38.*
Lazar E, et al. Mol Cell Biol. Mar. 1988; 8 (3): 1247-52.*
Houdebine LM. J Biotechnol. May 31, 1994; 34 (3): 269-87.*
Verma IM, et al. Nature. Sep. 18, 1997; 389 (6648): 239-42.*
Patterson AP, Memorandum (Jan. 14, 2003); pp. 3.*
Pandha HS, et al. Cur Opin Invest Drugs. 2000; 1 (1): 122-34.*
Amalfitano A, et al. Cur Gene Ther. 2002; 2: 111-33.*
Rogemond V, et al. Clin Rev Allergy Immunol. Aug. 2000; 19 (1): 51-9.*
Honnorat J, et al. Eur. J. Neurosci. Dec. 1999; 11 (12): 4226-32.*
Thompson D, et al. Biotechniques. May 1992; 12 (5): 656-8.*

* cited by examiner

*Primary Examiner*—Stephen L. Rawlings
(74) *Attorney, Agent, or Firm*—B. Aaron Schulman; Stites & Harbison, PLLC

(57) ABSTRACT

The invention concerns a purified polypeptide, biologically active polypeptide derivative or fragment of said purified polypeptide, comprising an amino acid sequence selected among SEQ.ID. No. 2, No. 4, No. 6 and No. 8.

3 Claims, 24 Drawing Sheets

Molecular
weight scale +  —

66 kDa —

66kDa —

66kDa —

Molecular
weight scale

ULIP family

66kDa —

CV₂ antigen (POP 66/ULIP4)

Ulip2 mouse

```
                                                    M   S   Y   Q   G   K   K   N   I   P   P   I    12
ctcctcccgccccccggagag ATG TCT TAT CAG GGG AAG AAA AAT ATT CCA CCC ATC              58

T   S   D   R   L   L   I   K   G   G   K   I   V   N   D   D   Q   S   30
ACG AGC GAT CGT CTT CTG ATC AAA GGT GGC AAG ATT GTG AAT GAT GAC CAG TCC          112

F   Y   A   D   I   Y   M   E   D   G   L   I   K   Q   I   G   E   N   48
TTC TAT GCA GAC ATA TAC ATG GAA GAT GGG TTG ATC AAG CAA ATA GGA GAA AAC          166

L   I   V   P   G   G   V   K   T   I   E   A   H   S   R   M   V   I   66
CTG ATT GTA CCA GGA GGG GTG AAG ACC ATC GAA GCC CAC TCC AGA ATG GTG ATT          220

P   G   G   I   D   V   H   T   R   F   Q   M   P   D   Q   G   M   T   84
CCC GGA GGA ATT GAC GTG CAT ACT CGC TTC CAG ATG CCT GAC CAG GGA ATG ACA          274

S   A   D   F   F   K   T   G   T   K   A   A   L   A   G   G   T   T  102
TCC GCT GAT TTC TTC CAG ACC GGA ACC AAG GCC GCC CTG GCC GGG GGA ACC ACC          328

M   I   I   D   H   V   V   P   E   P   G   T   S   L   L   A   A   F  120
ATG ATC ATT GAC CAT GTT GTT CCT GAG CCC GGG ACG AGC CTA TTG GCT GCC TTT          382

D   Q   W   R   E   W   A   D   S   K   S   C   C   D   Y   S   L   H  138
GAT CAG TGG AGG GAG TGG GCT GAC AGC AAG TCC TGC TGT GAC TAT TCG CTG CAC          436

V   D   I   T   E   W   H   K   G   I   Q   E   E   M   E   A   L   V  156
GTG GAC ATC ACT GAG TGG CAC AAG GGC ATC CAG GAG GAG ATG GAA GCT CTG GTG          490
```

```
K   D   H   G   V   N   S   F   L   V   Y   M   A   F   K   D   R   F     174
AAG GAC CAC GGG GTA AAC TCC TTC CTC GTG TAC ATG GCT TTC AAA GAT CGA TTC   544

Q   L   T   D   S   Q   I   Y   E   N   A   H   V   I   A   E   Q   G     192
CAG CTG ACG GAT TCC CAG ATC TAT GAA AAT GCA CAC GTG ATC GCT GAG CAG GGT   598

A   I   Q   V   H   A   E   A   E   N   G   D   I   I   A   R   D   Q     210
GCC ATA CAA GTC CAC GCA GAG GCA GAG AAT GGT GAC ATC ATT GCT CGG GAT CAG   652

R   I   L   D   S   V   N   G   P   E   D   I   H   V   L   S   R   P     228
AGG ATC CTG GAT TCC GTG AAC GGC CCC GAG GAC ATC CAC GTG TTG AGC CGG CCA   706

E   V   E   A   Y   V   E   R   S   I   T   I   A   N   Q   T             246
GAG GTC GAA GCT TAT GTG GAA CGG TCC ATC ACT ATT GCC AAC CAG ACC           760

N   C   P   L   Y   V   K   T   G   S   E   A   A   P   I   K   A   A     264
AAC TGC CCT CTG TAT GTC AAA ACC GGA AGT GAG GCT GCG CCC ATC AAG GCG ATC   814

A   Q   A   R   K   G   V   V   Y   G   N   W   T   I   T   A   A   S     282
GCT CAG GCA CGG AAG GGA ACT GTG TAT GGT AAC TGG ACG ATC ACG GCC AGC AGC   868

L   G   T   D   G   S   H   Y   W   S   K   N   D   P   T   K   A   A     300
CTG GGG ACT GAT GGC TCT CAT TAC TGG AGC AAG AAC GAC CCA ACC AAG GCT GCG   922

F   V   T   P   L   S   P   D   L   Q   V   T   D   F   C   A   H   L     318
TTT GTC ACC CCA TTG AGC CCC GAC CTC CAA GTC ACT GAC TTT TGC GCA CAC CTC   976

S   L   C   G   D   L   Q   G   V   T   G   S   A   H   C   T   F        336
TCG TTG TGT GGA GAC CTC CAA GGA GTC ACT GGC AGT GCC CAC TGC ACC TTC      1030
```

| N AAC | T ACT | A GCC | Q CAG | K AAG | V GTG | G GGG | K AAG | D GAC | N AAC | F TTC | T ACC | L TTG | I ATT | P CCC | E GAG | G GGC | 354 1084 |
| T ACC | N AAC | G GGC | E GAG | E GAG | R CGG | M ATG | S TCT | I ATT | W TGG | D GAT | K AAA | A GCT | V GTG | T ACT | 372 1138 |
| G GGG | K AAG | M ATG | D GAT | E GAG | N AAT | Q CAG | F TTT | V GTG | A GCT | T ACC | S AGC | N AAC | A GCA | V GTC | A GCC | K AAA | 390 1192 |
| V GTC | F TTC | N AAC | L CTT | Y TAC | P CCC | R CGG | K AAA | G GGT | R CGC | I ATC | S TCG | V GTG | S TCT | D GAT | A GCT | D GAC | 408 1246 |
| L TTG | V GTC | I ATC | W TGG | D GAC | P CCT | D GAC | S AGT | V GTG | K AAG | I ATC | T ACC | A GCC | K AAG | H CAC | N AAC | 426 1300 |
| S AGT | A GCT | L CTT | E GAG | Y TAC | N AAC | I ATC | F TTT | E GAA | M ATG | G GGC | R CGC | C TGT | G GGC | S TCC | P CCA | L CTG | 444 1354 |
| V GTC | V GTC | I ATC | S AGC | Q CAG | G GGC | K AAG | I ATT | V GTC | L CTG | E GAG | D GAC | G GGC | T ACA | L CTT | H CAT | V GTC | T ACT | 462 1408 |
| E GAA | G GGC | S TCA | R CGC | Y TAC | I ATT | P CCC | R CGG | K AAG | E GAG | P CCT | F TTC | D GAC | F TTT | V GTG | Y TAC | K AAA | 480 1462 |
| R CGC | I ATC | K AAA | A GCA | R AGG | S AGC | R AGG | L CTG | A GCT | E GAG | L CTG | R AGA | G GGG | V GTC | P CCT | R CGT | G GGC | L CTG | 498 1516 |
| Y TAT | D GAC | G GGA | P CCG | V GTA | C TGC | E GAG | V GTG | S TCT | T ACG | V GTG | K AAG | P CCC | T ACG | V GTG | T ACT | P CCA | A GCC | 516 1570 |

FIG. 9C

|  |  | S | S | A | K | T | S | P | A | K | Q | Q | A | P | P | V | R | N | L | 534 |
|---|---|---|---|---|---|---|---|---|---|---|---|---|---|---|---|---|---|---|---|---|
|  |  | TCA | TCA | GCT | AAG | ACA | TCC | CCT | GCC | AAG | CAG | CAG | GCA | CCA | CCT | GTT | CGG | AAC | CTG | 1624 |
|  |  | H | Q | S | G | F | S | L | S | G | A | Q | I | D | N | I | P | R | 552 |
|  |  | CAC | CAG | TCT | GGA | TTC | AGC | TTG | TCT | GGT | GCT | CAG | ATT | GAC | AAC | ATT | CCC | CGC | 1678 |
|  |  | R | T | T | Q | R | I | V | A | P | P | G | R | A | N | I | T | S | 570 |
|  |  | CGC | ACC | ACC | CAG | CGC | ATC | GTG | GCA | CCC | CCT | GGT | CGT | GCC | AAC | ATC | ACC | AGC | 1732 |
|  |  | L | G | * |  |  |  |  |  |  |  |  |  |  |  |  |  |  | 573 |
|  |  | CTG | GGC | TAA | agccctaggcctgcaggccacttggggatggggacacctgaggacattctga | | | | | | | | | | | | | | 1800 | gacttccttcttccat

FIG. 9D

Ulip3 mouse

```
gctgtctgtcttcagcgccctcctctcgcctctcccctgcctctccctccctcctccctccttgccaagccggc         72
ggtgcaggcagccggagcggcgggagcagcgggagtgggcagcggtgggagccgagcttctg                    144
tccttctttcatccctccctgccttgtcgccgctctcacgatagccgccgggagagacccgggtag                216
                                                           M  S  H  Q              4
agcgccaggcagacgttagttccagcggccggaggctccagaggggcc ATG TCT CAT CAG                  281

G   K   K   S   I   P   H   I   T   S   D   R   L   L   I   R   G   G            22
GGG AAG AAG AGC ATC CCG CAC ATC ACC AGT GAC CGG CTC CTC ATC AGA GGT GGA           335

R   I   N   D   D   Q   S   F   Y   A   D   V   P   I   G   D   G               40
CGC ATC AAT GAT GAC CAG TCC TTC TAC GCC GAT GTC CCT ATT GGT GAT GGA               389

L   I   K   Q   I   G   E   N   L   I   V   G   V   K   T   I               58
CTC ATA AAA CAA ATA GGA GAG AAC CTG ATT GTT GGA GTG AAG ACC ATC                   443

E   A   N   G   R   M   V   I   D   D   F   F   Q   T   Y   L               76
GAG GCG AAT GGC CGA ATG GTC ATT GAT GAC TTC TTC CAG ACT TAC CTG                   497

Q   K   P   S   Q   M   T   S   A   D   I   D   H   V   P   E   P   K           94
CAG AAG CCC TCC CAG ATG ACC TCG GCT GAT ATT GAC CAC GTT CCT GAA CCT AAA          551

A   L   A   G   G   T   M   F   E   K   W   H   E   A   A   D   T              112
GCA GCG CTG GCA GGT GGA ACC ATG TTT GAG AAA TGG CAC GAA GCA GCA GAC ACC           605

G   S   S   L   T   S   F   K   K                                              130
GGG TCC AGC CTG ACT TCC TTT                                                      659
```

FIG. 10A

| | | | | | | | | | | | | | | | | | |
|---|---|---|---|---|---|---|---|---|---|---|---|---|---|---|---|---|---|
| S | C | C | D | Y | S | L | H | V | D | I | T | S | W | Y | D | G | V | 148 |
| TCC | TGC | TGT | GAC | TAT | TCC | CTC | CAC | GTG | GAC | ATC | ACA | AGC | TGG | TAT | GAT | GGT | GTT | 713 |
| R | E | E | L | E | V | L | V | Q | D | K | G | V | N | S | F | Q | V | 166 |
| CGG | GAA | GAG | CTG | GAG | GTG | CTG | GTG | CAG | GAC | AAA | GGT | GTC | AAC | TCC | TTC | CAA | GTC | 767 |
| Y | M | A | Y | K | D | L | Y | Q | M | S | D | L | Y | E | A | 184 |
| TAC | ATG | GCG | TAT | AAG | GAC | CTG | TAC | CAG | ATG | TCT | GAC | CTG | TAT | GAA | GCC | 821 |
| F | T | F | L | K | G | L | G | A | V | I | L | H | A | E | N | G | 202 |
| TTC | ACC | TTC | CTT | AAG | GGT | TTG | GGA | GCT | GTC | ATC | TTA | CAT | GCA | GAA | AAT | GGA | 875 |
| D | L | I | A | Q | E | K | R | I | L | E | M | E | A | L | E | N | G | 220 |
| GAT | TTG | ATA | GCT | CAG | GAA | AAA | CGG | ATC | CTG | GAG | ATG | GAG | GCC | CTG | GAG | AAT | GGA | 929 |
| E | G | H | A | L | S | R | P | E | N | C | P | E | A | V | I | T | G | P | 238 |
| GAG | GGT | CAT | GCT | CTG | AGC | AGA | CCC | GAG | AAT | TGC | CCT | GAG | GCC | GTG | ATC | ACG | GGT | CCC | 983 |
| A | I | A | G | R | D | I | I | A | L | A | R | K | Y | E | A | V | F | R | 256 |
| GCT | ATT | GCA | GGC | CGG | GAC | ATC | ATC | GCA | CTG | GCC | AGG | AAA | TAC | GAG | GCT | GTG | TTC | CGG | 1037 |
| S | K | S | A | A | A | L | G | T | D | G | T | K | P | L | V | M | 274 |
| AGC | AAG | AGT | GCA | GCG | GAC | CTG | GGA | ACC | GAT | GGC | ACC | AAG | CCT | CTT | GTC | ATG | 1091 |
| F | G | E | P | I | A | A | S | P | H | Y | W | P | L | S | V | 292 |
| TTC | GGT | GAG | CCC | ATA | GCC | GCT | AGC | CCT | CAC | TAC | TGG | CCT | CTG | AGC | AGC | 1145 |
| K | N | W | A | K | A | A | A | F | V | T | S | P | P | L | S | D | 310 |
| AAG | AAC | TGG | GCC | AAG | GCA | GCA | GCT | TTT | GTG | ACT | TCC | CCT | CCC | CTG | AGC | CCA | GAC | 1199 |

FIG. 10B

```
P   T   T   P   D   Y   L   T   S   L   L   A   C   G   D   L   Q   V    328
CCC ACC ACT CCT GAC TAC TTG ACC TCC TTG CTG GCC TGT GGA GAC TTG CAG GTC  1253

T   G   S   H   C   P   Y   S   I   A   Q   K   A   V   G   K   D       346
ACA GGT AGT CAC TGT CCC TAC AGT ATT GCT CAG AAG GCT GTG GGC AAG GAC     1307

N   F   T   L   I   P   E   G   V   N   G   I   E   E   R   M   T   V   364
AAC TTC ACT CTG ATC CCT GAG GGT GTC AAT GGT ATA GAA GAG CGG ATG ACC GTT 1361

V   W   D   K   A   V   A   T   G   K   M   D   E   N   Q   F   V   A   382
GTC TGG GAC AAG GCA GTG GCT ACT GGC AAG ATG GAT GAG AAC CAG TTT GTA GCC 1415

V   T   S   N   A   K   I   F   N   L   Y   P   R   K   G   R           400
GTC ACC AGC AAC GCA GCC ATC TTC AAC CTG TAC CCG AGG AAA GGT CGG         1469

I   A   V   G   S   D   A   D   V   I   W   D   P   Y   N   I   F   E   418
ATC GCT GTG GGC TCC GAT GCT GAT GTC ATC TGG GAC CCA TAC AAC ATC TTT GAG 1523

T   I   T   A   K   S   H   P   L   V   T   V   E   S   Q   G   M   K   436
ACC ATA ACA GCC AAA AGC CAT CCC CTG GTG ACT GTG GAG AGT CAG GGC ATG AAG 1577

M   E   C   H   G   N   I   S   V   S   K   G   L   V   I   K   P   R   454
ATG GAG TGC CAC GGC AAC ATC AGT GTG TCC AAG GGC CTG GTC ATC AAG CCT CGG 1631

E   D   G   N   A   K   S   V   G   M   G   R   F   Q   R   S   R   K   472
GAG GAT GGA AAC GCC AGT GTC AGC ATG GGC CGC TTC CAG CGG AGC AGA AAG     1685

P   F   P   E   H   L   Y   Q   R   V   I   R   S   K   V   F   G       490
CCA TTC CCA GAG CAT CTC TAC CAG CGT GTC ATC AGG AGC AAG GTT TTC GGG     1739
```

FIG. 10C

| | | | | | | | | | | |
|---|---|---|---|---|---|---|---|---|---|---|
| L | H | S | V | S | R | G | M | Y | D | G | P | V | Y | E | V | P | A | 508 |
| TTG | CAT | AGT | GTT | TCC | AGG | GGC | ATG | TAC | GAT | GGG | CCT | GTG | TAC | GAG | GTG | CCA | GCT | 1793 |
| T | P | K | H | A | A | P | A | P | S | A | E | S | S | P | S | K | H | 526 |
| ACA | CCC | AAA | CAT | GCT | GCT | CCT | GCT | CCT | TCT | GCC | GAA | TCC | TCG | CCT | TCT | AAA | CAC | 1847 |
| Q | P | P | P | I | R | N | L | H | Q | S | N | F | S | L | S | G | A | 544 |
| CAA | CCC | CCA | CCC | ATC | CGG | AAC | CTC | CAC | CAG | TCC | AAC | TTC | AGC | TTA | TCA | GGT | GCC | 1901 |
| Q | I | D | D | N | N | P | R | R | T | R | H | R | I | V | A | P | P | 562 |
| CAG | ATA | GAT | GAC | AAC | AAT | CCA | AGG | CGT | ACA | AGG | CAC | CGC | ATT | GTG | GCG | CCC | CCT | 1955 |
| G | G | R | S | N | I | T | S | L | G | * | | | | | | | | 573 |
| GGT | GGC | CGC | TCC | AAC | ATC | ACC | AGC | CTC | GGT | TGA | cctcagatgagccagatatgcaagagt | | | | | | | 2015 |

```
gaaggattatgggaaaacgtccattccttttcgtgttttgaagcccacagtttagttggtactgacgga     2087
ggggagattgagcgatgctctttcctttctgtttaggaagaagtggtactagtgtggtgttgcctgga     2159
agtccctcgcccacagtgtgttcacaccgactccacctcagagcatggtgccgtccgttttccttccta   2231
gtgacccaggtttagcatcgtcctatactgttccctccactcctccatgaccctctgagtgatgg       2297
```

FIG. 10D

Ulip4 mouse

```
gctgactaatatgcttaaattcagcggggtcgccacgtctggtcggtacgtccacgcccgcgcagccctacc                    72
                          M   S   F   Q   G   K   K   S   I   P                              10
gaggacactcagcccgccgtgtatcagg ATG TCC TTC CAA GGC AAG AAG AGC ATT CCC                         131

R   I   T   S   D   R   L   L   I   K   G   K   I   V   N   D   D                           28
CGG ATA ACG AGC GAC CGC CTT CTC ATC AAA GGT GGG AAG ATT GTG AAC GAT GAC                      185

Q   S   F   H   A   D   L   Y   V   E   D   G   L   I   K   Q   I   G                       46
CAG TCC TTT CAT GCT GAT CTG TAT GTG GAA GAC GGT CTG ATT AAA CAA ATT GGA                      239

E   N   L   I   V   P   G   G   I   T   I   K   T   I   D   A   H   M                       64
GAA AAT CTC ATC GTC CCT GGG GGC ATC ACC AAA ACC ATC GAT GCT CAT GGC CTG ATG                  293

V   L   P   G   G   V   D   F   C   Q   H   T   R   L   Q   M   P   V   M   G               82
GTG CTG CCT GGG GGA GTT GAC TTC TGT CAG CAC ACC CGG CTG CAG ATG CCT GTG ATG GGC              347

M   T   P   A   D   D   V   H   V   F   P   D   T   K   A   A   L   A   G   G              100
ATG ACC CCA GCT GAT GAT GTG TTT CCT GAC ACC AAG GCG GCT CTA GCA GGC GGG                      401

T   T   M   I   I   D   H   R   D   G   A   D   S   A   A   C   V   S   L   A              118
ACC ACC ATG ATA ATA TTG GAC CAT CGG CGG GGA GAC AGC GCG GCC TGC GTG AGC CTG GCA              455

A   Y   E   Q   W   R   E   P   D   G   A   A   C   D   Y   E   K   G                      136
GCC TAT GAG CAG TGG CGG GAG CCT GAC GGA GCA GCC TGT TGT GAC TAC TCC                          509

L   H   V   D   I   P   R   W   H   E   S   T   K   E   L   E   A                           154
TTA CAT GTG GAC ATT CCT CGC TGG CAC GAG AGC ACC AAA GAA GAG CTG GAG GCC                      563
```

FIG. 11A

```
L   V   R   D   K   G   V   N   S   F   L   V   F   M   A   Y   K   D    172
CTA GTC AGG GAC AAA GGT GTG AAC TCC TTC CTG GTC TTC ATG GCA TAC AAG GAC  617

R   C   Q   T   D   G   I   Y   E   I   F   S   L   I   R   D            190
AGG TGC CAG ACT GAC GGT ATA TAT GAA ATC TTC AGC CTC ATC CGG GAC          671

L   G   A   V   Q   H   V   A   E   N   G   I   D   V   F   M   E   E    208
CTG GGA GCT GTG CAG CAC GTG GCA GAA AAT GGG ATC GAC GTC TTC ATG GAG GAA  725

Q   R   L   L   E   Q   I   T   G   I   P   E   G   H   V   L   S        226
CAG CGC CTG CTG GAG CAA ATC ACT GGT ATC CCT GAG GGC CAT GTG CTC AGC      779

H   P   E   E   V   A   E   A   V   Y   R   A   V   T   I   A   K        244
CAC CCA GAA GAG GTA GAG GCC GCT GTG TAC AGA GCA GTC ACC ATT GCC AAG      833

Q   A   N   C   Y   L   P   Y   K   V   M   S   K   V   V   A   D        262
CAG GCC AAC TGC TAC CTA CCA TAC AAG GTG ATG AGC AAG GTG GTG GCA GAC      887

M   V   A   Q   G   R   H   G   S   V   F   G   E   P   I   T            280
ATG GTT GCC CAA GGC AGG CAC GGG TCA GTC TTT GGG GAA CCT ATC ACT          941

A   S   L   G   T   D   G   S   H   Y   W   N   P   T   K   A            298
GCC AGC CTG GGC ACT GAT GGC TCA CAC TAC TGG AAC CCT ACT AAG AAG GCT      995

A   A   F   V   T   S   P   I   N   Q   L   T   A   D   H              316
GCA GCC TTT GTC ACT TCA CCC ATC AAC AAC CCG CAG ACA ACT GCA GAC CAC     1049

L   T   S   L   L   S   S   G   D   L   V   T   G   S   A   H   C       334
CTC ACC TCT CTG CTG TCC AGT GGG GAC CTC CAG CTG GTG ACA GGC AGT GCC CAC TGC  1103
```

FIG. 11B

| T   | F   | T   | T   | A   | Q   | K   | A   | V   | G   | K   | D   | N   | F   | T   | L   | I   | P   | 352  |
| ACC | TTC | ACT | ACT | GCC | CAG | AAG | GCT | GTT | GGC | AAA | GAC | AAC | TTC | ACA | CTG | ATC | CCC | 1157 |
| E   | V   | N   | G   | I   | E   | E   | R   | M   | S   | V   | V   | W   | E   | K   | C   | N   | A   | 370  |
| GAG | GTA | AAC | GGT | ATA | GAA | GAG | CGC | ATG | TCT | GTC | GTG | TGG | GAG | AAA | TGT | AAT | GCT | 1211 |
| A   | S   | G   | K   | M   | D   | E   | E   | F   | V   | A   | V   | T   | S   | T   | N   | A   | D   | 388  |
| GCT | TCA | GGG | AAA | ATG | GAC | GAG | AAT | TTC | GTT | GCC | GTG | ACC | AGC | ACA | AAT | GCT | GAT | 1265 |
| A   | K   | I   | F   | N   | Y   | P   | R   | K   | G   | R   | V   | A   | V   | G   | S   | K   | D   | 406  |
| GCC | AAA | ATC | TTC | AAT | TAC | CCC | AGG | AAG | GGG | CGT | GTG | GCC | GTG | GGC | TCT | AAG | GAT | 1319 |
| A   | D   | L   | V   | I   | W   | N   | P   | R   | A   | T   | K   | V   | I   | S   | A   | K   | S   | 424  |
| GCT | GAC | CTG | GTC | ATC | TGG | AAC | CCC | AGG | GCC | ACG | AAA | GTC | ATC | TCT | GCC | AAG | AGC | 1373 |
| H   | N   | L   | N   | V   | E   | Y   | I   | F   | E   | G   | V   | E   | G   | R   | G   | V   | V   | 442  |
| CAT | AAC | CTG | AAT | GTA | GAG | TAC | ATC | TTT | GAA | GGA | GTG | GAG | TGC | CGA | GGA | GTG | GTG | 1427 |
| P   | T   | V   | I   | S   | Q   | R   | G   | V   | V   | L   | E   | D   | G   | N   | L   | L   | L   | 460  |
| CCC | ACG | GTG | ATA | AGT | CAG | AGA | GGC | GTG | GTG | CTG | GAG | GAC | GGA | AAC | CTG | CTG | CTT | 1481 |
| V   | T   | P   | G   | A   | R   | F   | I   | P   | R   | K   | T   | F   | P   | D   | N   | F   | V   | 478  |
| GTC | ACT | CCA | GGG | GCT | CGG | TTC | ATT | CCC | AGG | AAG | ACG | TTC | CCG | GAC | AAC | TTT | GTC | 1535 |
| Y   | K   | R   | I   | K   | A   | R   | N   | R   | L   | A   | E   | I   | H   | G   | V   | P   | R   | 496  |
| TAT | AAG | AGG | ATA | AAG | GCT | CGC | AAC | AGG | CTA | GCA | GAG | ATC | CAC | GGT | GTG | CCT | CGA | 1589 |

FIG. 11C

```
  G   L   Y   D   G   P   V   H   E   V   M   L   P   A   K   P   G   S    514
GGC CTG TAC GAC GGG CCT GTG CAT GAA GTG ATG TTA CCT GCC AAG CCA GGA AGT   1643

G   T   Q   A   R   A   S   C   S   G   K   I   S   V   P   P   V   R    532
GGC ACA CAG GCC CGT GCA TCC TGT TCA GGC AAG ATC TCA GTG CCA CCC GTG CGC   1697

N   L   H   Q   Q   S   G   F   S   L   S   Q   A   D   D   H   I        550
AAC CTG CAC CAG CAG TCG GGG TTC AGC CTA TCT CAG GCT GAC GAT CAC ATT       1751

A   R   R   T   A   Q   K   I   M   A   P   P   G   R   S   N   I        568
GCC AGA CGT ACG GCT CAG AAG ATC ATG GCA CCC CCC GGA CGC TCC AAC ATC       1805

T   S   L   S   *                                                         573
ACG TCT CTT TCC TAG  actttggggtctttggcaagctgtgctgtcccactggcagggtgtggggac  1871 gactcacgtcagttagctcctttgtagattgttattgtgaaaggc                             1920
```

FIG. 11D

Ulip4 human

```
                                                     M   S   F   Q   G   K   K   S   I   P    10
GCCGCCCCTACCAGAGACCCCCAGGAGCAGG ATG TCC TTC CAG GGC AAG AAA AGC ATC CCC     61

R   I   T   S   D   R   L   L   I   R   G   R   I   V   N   D           28
CGG ATC ACG AGT GAC CGC CTT CTG ATC AGA GGT AGG ATC GTG AAT GAC          115

Q   S   F   Y   A   D   V   H   V   E   D   G   L   I   K   Q   I   G    46
CAG TCC TTT TAC GCT GAT GTG CAC GTG GAA GAT GGC TTG ATA AAA CAA ATC GGA   169

E   N   L   I   P   G   G   I   *   T   I   D   A   H   Q   L   M        64
GAA AAC CTC ATC CCT GGG GGC ATC TAG ACC ATT GAC GCC CAC CAA CTG ATG      223

V   L   P   G   G   V   D   F   C   Q   T   R   L   Q   M   P   L   G    82
GTC CTT CCT GGT GGC GTT GAC TTC TGT CAG ACA AGG CTG CAG CCT CTG GGC      277

M   T   P   A   D   F   H   V   K   Q   G   T   K   A   A   L   A   G   100
ATG ACA CCG GCT GAC TTC CAC GTC TGT CAG GGC ACC AAG GCA GCG CTA GGA      331

T   T   M   I   L   D   W   R   E   R   A   D   S   A   C   D   Y   S   118
ACC ACC ATG ATC TTG GAC TGG CGG GAG GCG GAC AGC AGC TGC GAC TAC TCC      385

A   Y   E   Q   W   R   E   R   A   D   S   A   C   D   Y   S          136
GCC TAC GAG CAG TGG CGG GAG GAG GCG GAC AGC AGC TGC GAC TAC TCC          439

L   H   V   D   I   T   R   W   H   E   S   I   K   E   L   E   A       154
CTG CAC GTG GAC ATC ACC CGA TGG CAT GAG AGC ATC AAG GAG CTG GAG GCC      493
```

FIG. 12A

```
L   V   L   K   E   K   G   V   N   S   F   L   V   F   M   A   Y   K   D    172
CTG GTC CTG AAG GAG AAG GGT GTG AAC TCC TTC CTG GTC TTC ATG GCA TAC AAG GAC  547

R   C   R   Q   S   D   S   Q   M   Y   E   I   F   S   I   R   D            190
CGG TGC CGG CAG TGC CAG AGC GAC AGC CAG ATG TAC GAG ATC TTC AGC ATC CGG GAC  601

L   G   A   L   Q   V   H   A   E   N   G   D   I   V   E   E              208
CTG GGG GCC TTG CAG GTG CAC GCT GAG AAC GGG GAC ATC GTG GAG GAG GAG GAG GAG  655

Q   K   R   L   E   L   T   G   P   E   G   H   V   L   S                  226
CAG AAG CGG TTG GAG CTC ACT GGC CCC GAG GGC CAC GTG CTC AGC AGC             709

H   P   E   E   V   A   E   Y   R   V   A   V   T   I   A   K              244
CAC CCC GAG GAG GTG GAG GCT GCG GTG CGA GCT GTC ACC ATC GCC AAG             763

Q   A   N   C   P   L   Y   V   K   M   S   K   G   A   A   D              262
CAG GCA AAC TGC CCG CTG TAC GTC ACC AAG GTG ATG AGC AAG GGG GCG GCC GAC      817

A   I   A   Q   R   K   G   V   V   F   E   N   W   K   P   A   I   T      280
GCT ATC GCT CAG CGC AAG AGA GGG GTG GTC TTT GGG AAC TGG GCC CCC ATC ACC      871

A   S   L   G   T   D   G   S   H   Y   V   W   S   D   T   A   K   D      298
GCC AGC CTG GGC ACC GAC GGT TCA CAC TAC TGG AGC GAC CCA ACC GCA AAG GAC     925

A   F   V   T   S   P   P   N   V   T   T   A   S                          316
GCA TTC GTC TCA CCC CCT GTC AAC CCC ACC ACG GCA GAC CAC                    979

L   C   L   S   S   G   L   Q   D   V   T   G   S   A   H   C              334
CTC ACC TGC TTG CTG TCC AGC GGG GAC CTC CAG ACA GTG ACA GGC AGC GCC CAC TGC 1033
```

| G | L | Y | D | G | P | V | H | E | V | M | V | P | A | K | P | G | S | 514 |
| --- | --- | --- | --- | --- | --- | --- | --- | --- | --- | --- | --- | --- | --- | --- | --- | --- | --- | --- |
| GGG | CTG | TAT | GAC | GGG | CCC | GTC | CAC | GAG | GTG | ATG | GTG | CCT | GCC | AAG | CCA | GGG | AGT | 1573 |
| G | A | P | A | R | A | S | C | P | G | I | K | S | V | P | P | V | R | 532 |
| GGC | GCT | CCG | GCC | CGC | GCG | TCC | TGC | CCA | GGC | AAG | ATC | TCC | GTG | CCT | CCT | GTG | CGC | 1627 |
| N | L | H | Q | S | G | F | S | L | S | G | S | Q | A | D | D | H | I | 550 |
| AAC | CTA | CAT | CAG | TCG | GGG | TTC | AGC | CTA | TCT | GGG | TCT | CAG | GCT | GAT | GAC | CAC | ATC | 1681 |
| A | R | R | | | | | | | | | | | | | | | | 553 |
| GCC | CGA | CGC | | | | | | | | | | | | | | | | 1690 |

FIG. 12D

SEQUENCE LISTING

```
<160> NUMBER OF SEQ ID NOS: 40

<210> SEQ ID NO 1
<211> LENGTH: 1817
<212> TYPE: DNA
<213> ORGANISM: Mus musculus

<400> SEQUENCE: 1
cttcctcccg ccccccggag agatgtctta tcaggggaag aaaaatattc cacccatcac      60
gagcgatcgt cttctgatca aaggtggcaa gattgtgaat gatgaccagt ccttctatgc     120
agacatatac atggaagatg ggttgatcaa gcaaatagga gaaaacctga ttgtaccagg     180
aggggtgaag accatcgaag cccactccag aatggtgatt cccggaggaa ttgacgtgca     240
tactcgcttc cagatgcctg accagggaat gacatccgct gatgacttct tccagggaac     300
caaggcggcc ctgccggggg gaaccaccat gatcattgac catgttgttc ctgagcccgg     360
gacgagccta ttggctgcct ttgatcagtg gagggagtgg gctgacagca agtcctgctg     420
tgactattcg ctgcacgtgg acatcactga gtggcacaag ggcatccagg aggagatgga     480
agctctggtg aaggaccacg gggtaaactc cttcctcgtg tacatggctt tcaaagatcg     540
attccagctg acggattccc agatctatga agtgctgagc gtgatccggg atatcggtgc     600
catagctcaa gtccacgcag agaatggtga catcattgct gaggcacagc agaggatcct     660
ggatctgggc atcacgggcc ccgagggaca cgtgttgagc cggccagagg aggtcgaggc     720
tgaagctgtg aaccggtcca tcactattgc caaccagacc aactgccctc tgtatgtcac     780
caaagtgatg cccaagagtg cggctgaagt catcgctcag gcacggaaga agggaactgt     840
ggtgtatggt gagcccatca cggccagcct ggggactgat ggctctcatt actggagcaa     900
gaactgggcc aaggctgcgg cctttgtcac ctccccaccc ttgagcccg  acccaaccac     960 tccagacttt ctcaactcgt tgctgtcctg tggagacctc caagtcactg gcagtgccca    1020
```

```
ctgcaccttc aacactgccc agaaggctgt ggggaaggac aacttcacct tgattcccga    1080
gggcaccaac ggcactgagg agcggatgtc tgtcatttgg gataaagctg tggtcactgg    1140
gaagatggat gagaatcagt tgtggctgt gaccagcacc aacgcagcca aagtcttcaa     1200
cctttacccc cggaaaggtc gcatctcggt gggatctgat gctgacttgg tcatctggga    1260
ccctgacagt gtgaagacca tctctgccaa gacacacaac agtgctcttg agtacaacat    1320 cttttgaaggc atggagtgtc gcggctcccc actggtggtc atcagccagg caagattgt    1380 cctggaggac ggcacacttc atgtcactga aggctcagga cgctacattc cccggaagcc    1440
cttccctgac tttgtgtaca aacgcatcaa agcaaggagc aggctggctg agctgagagg    1500
ggtccctcgt ggcctgtatg acggaccggt atgcgaggtg tctgtgacgc ccaagacggt    1560
gactccagcc tcatcagcta agacatcccc tgccaagcag caggcaccac ctgttcggaa    1620
cctgcaccag tctggattca gcttgtctgg tgctcagatt gacgacaaca ttccccgccg    1680
caccacccag cgcatcgtgg cacccctgg tggccgtgcc aacatcacca gcctgggcta    1740
aagcccctag gcctgcaggc cacttgggga tggggatgg gacacctgag gacattctga    1800
gacttccttt cttccat                                                   1817
```

<210> SEQ ID NO 2
<211> LENGTH: 572
<212> TYPE: PRT
<213> ORGANISM: Mus musculus

<400> SEQUENCE: 2

```
Met Ser Tyr Gln Gly Lys Lys Asn Ile Pro Pro Ile Thr Ser Asp Arg
1               5                   10                  15

Leu Leu Ile Lys Gly Gly Lys Ile Val Asn Asp Asp Gln Ser Phe Tyr
            20                  25                  30

Ala Asp Ile Tyr Met Glu Asp Gly Leu Ile Lys Gln Ile Gly Glu Asn
        35                  40                  45

Leu Ile Val Pro Gly Gly Val Lys Thr Ile Glu Ala His Ser Arg Met
    50                  55                  60

Val Ile Pro Gly Gly Ile Asp Val His Thr Arg Phe Gln Met Pro Asp
65                  70                  75                  80

Gln Gly Met Thr Ser Ala Asp Asp Phe Phe Gln Gly Thr Lys Ala Ala
                85                  90                  95

Leu Ala Gly Gly Thr Thr Met Ile Ile Asp His Val Val Pro Glu Pro
            100                 105                 110

Gly Thr Ser Leu Leu Ala Ala Phe Asp Gln Trp Arg Glu Trp Ala Asp
        115                 120                 125

Ser Lys Ser Cys Cys Asp Tyr Ser Leu His Val Asp Ile Thr Glu Trp
    130                 135                 140

His Lys Gly Ile Gln Glu Glu Met Glu Ala Leu Val Lys Asp His Gly
145                 150                 155                 160

Val Asn Ser Phe Leu Val Tyr Met Ala Phe Lys Asp Arg Phe Gln Leu
                165                 170                 175

Thr Asp Ser Gln Ile Tyr Glu Val Leu Ser Val Ile Arg Asp Ile Gly
            180                 185                 190

Ala Ile Ala Gln Val His Ala Glu Asn Gly Asp Ile Ile Ala Glu Ala
        195                 200                 205

Gln Gln Arg Ile Leu Asp Leu Gly Ile Thr Gly Pro Glu Gly His Val
    210                 215                 220

Leu Ser Arg Pro Glu Glu Val Glu Ala Glu Ala Val Asn Arg Ser Ile
```

```
                225                 230                 235                 240
Thr Ile Ala Asn Gln Thr Asn Cys Pro Leu Tyr Val Thr Lys Val Met
                245                 250                 255
Pro Lys Ser Ala Ala Glu Val Ile Ala Gln Ala Arg Lys Lys Gly Thr
            260                 265                 270
Val Val Tyr Gly Glu Pro Ile Thr Ala Ser Leu Gly Thr Asp Gly Ser
            275                 280                 285
His Tyr Trp Ser Lys Asn Trp Ala Lys Ala Ala Phe Val Thr Ser
        290                 295                 300
Pro Pro Leu Ser Pro Asp Pro Thr Thr Pro Asp Phe Leu Asn Ser Leu
305                 310                 315                 320
Leu Ser Cys Gly Asp Leu Gln Val Thr Gly Ser Ala His Cys Thr Phe
                325                 330                 335
Asn Thr Ala Gln Lys Ala Val Gly Lys Asp Asn Phe Thr Leu Ile Pro
                340                 345                 350
Glu Gly Thr Asn Gly Thr Glu Glu Arg Met Ser Val Ile Trp Asp Lys
            355                 360                 365
Ala Val Val Thr Gly Lys Met Asp Glu Asn Gln Phe Val Ala Val Thr
        370                 375                 380
Ser Thr Asn Ala Ala Lys Val Phe Asn Leu Tyr Pro Arg Lys Gly Arg
385                 390                 395                 400
Ile Ser Val Gly Ser Asp Ala Asp Leu Val Ile Trp Asp Pro Asp Ser
                405                 410                 415
Val Lys Thr Ile Ser Ala Lys Thr His Asn Ser Ala Leu Glu Tyr Asn
                420                 425                 430
Ile Phe Glu Gly Met Glu Cys Arg Gly Ser Pro Leu Val Val Ile Ser
            435                 440                 445
Gln Gly Lys Ile Val Leu Glu Asp Gly Thr Leu His Val Thr Glu Gly
        450                 455                 460
Ser Gly Arg Tyr Ile Pro Arg Lys Pro Phe Pro Asp Phe Val Tyr Lys
465                 470                 475                 480
Arg Ile Lys Ala Arg Ser Arg Leu Ala Glu Leu Arg Gly Val Pro Arg
                485                 490                 495
Gly Leu Tyr Asp Gly Pro Val Cys Glu Val Ser Val Thr Pro Lys Thr
            500                 505                 510
Val Thr Pro Ala Ser Ser Ala Lys Thr Ser Pro Ala Lys Gln Gln Ala
        515                 520                 525
Pro Pro Val Arg Asn Leu His Gln Ser Gly Phe Ser Leu Ser Gly Ala
        530                 535                 540
Gln Ile Asp Asp Asn Ile Pro Arg Arg Thr Thr Gln Arg Ile Val Ala
545                 550                 555                 560
Pro Pro Gly Gly Arg Ala Asn Ile Thr Ser Leu Gly
                565                 570

<210> SEQ ID NO 3
<211> LENGTH: 2297
<212> TYPE: DNA
<213> ORGANISM: Mus musculus

<400> SEQUENCE: 3
gctgtctgtc ttcagcgccc tcctctcgcc ctgcctctcc ctcctcctcc cgccctcctt      60
gccaagccgg gcggtgcagg cagccggagc agcggcggcg ggccgagcag cggggagtgg     120
gcagcggtgg gagccgagct tctgtccttt ctttcatccc tccctggcct tgtcgccgc     180
```

-continued

| | |
|---|---|
| tctcacgagt agcgccgccg ggagagaccc gggtagagcg ccaggcagac gttagttcca | 240 |
| gcggccgggc ggagggctcc agaggggcca tgtctcatca ggggaagaag agcatcccgc | 300 |
| acatcaccag tgaccggctc ctcatcagag gtggacgcat catcaatgat gaccagtcct | 360 |
| tctacgccga tgtctaccta aagatggac tcataaaaca aataggagag aacctgattg | 420 |
| ttcctggtgg agtgaagacc atcgaggcga atggccgaat ggtcattccc ggtggcattg | 480 |
| atgtcaacac ttacctgcag aagccctccc agggcatgac ctcggctgat gacttcttcc | 540 |
| agggcactaa agcagcgctg gcaggtggaa ccacgatgat cattgaccac gttgttcctg | 600 |
| aacctgggtc cagcttgttg acttcctttg agaaatggca cgaagcagca gacaccaaat | 660 |
| cctgctgtga ctattccctc cacgtggaca tcacaagctg gtatgatggt gttcgggaag | 720 |
| agctggaggt gctggtgcag acaaaggtg tcaactcctt ccaagtctac atggcgtata | 780 |
| aggacctgta ccagatgtct gacagccagc tgtatgaagc cttcaccttc cttaagggtt | 840 |
| tgggagctgt gatcttagtc catgcagaaa atggagattt gatagctcag gaacaaaaac | 900 |
| ggatcctgga gatgggcatc acgggtcccg agggtcatgc tctgagcaga cccgaggagc | 960 |
| tggaggccga ggctgtgttc cgggctattg ccattgcagg ccggatcaat tgccctgtgt | 1020 |
| acatcaccaa ggtcatgagc aagagtgcag cggacatcat cgcactggcc aggaagaaag | 1080 |
| gccctcttgt cttcggtgag cccatagccg ccagcctggg aaccgatggc acccactact | 1140 |
| ggagcaagaa ctgggccaag gcagctgcat ttgtgacttc ccctcccctg agcccagacc | 1200 |
| ccaccactcc tgactacttg acctccttgc tggcctgtgg agacttgcag gtcacaggta | 1260 |
| gtggccactg tccctacagt attgctcaga aggctgtggg caaggacaac ttcactctga | 1320 |
| tccctgaggg tgtcaatggt atagaagagc ggatgaccgt tgtctgggac aaggcagtgg | 1380 |
| ctactggcaa gatggatgag aaccagtttg tagccgtcac cagcaccaac gcagccaaga | 1440 |
| tcttcaacct gtacccgagg aaaggtcgga tcgctgtggg ctccgatgct gacgtagtca | 1500 |
| tctgggaccc agataagatg aagaccataa cagccaaaag ccataaatca actgtggagt | 1560 |
| acaacatctt tgagggcatg gagtgccacg gctcccccct ggtggtcatc agtcagggca | 1620 |
| agattgtctt tgaggatgga acatcagtg tcagcaaggg catgggccgc ttcatccctc | 1680 |
| ggaagccatt cccagagcat ctctaccagc gtgtcaggat cagaagcaag gttttcgggt | 1740 |
| tgcatagtgt ttccaggggc atgtacgatg ggcctgtgta cgaggtgcca gctacaccca | 1800 |
| aacatgctgc tcctgctcct tctgccgaat cctcgccttc taaacaccaa ccccacccca | 1860 |
| tccggaacct ccaccagtcc aacttcagct tatcaggtgc ccagatagat gacaacaatc | 1920 |
| caaggcgtac aggccaccgc attgtggcgc cccctggtgg ccgctccaac atcaccagcc | 1980 |
| tcggttgacc tcagatgagc cagatatgca agagtgaagg attatgggaa aacgtccatt | 2040 |
| cctttttccgt gttttgaag cccacagttt tagttggtac tgacggaggg gagattgagc | 2100 |
| gatgctcttt ccttctctgt ttaggaagaa gtggtactag tgtggtgtgt ttgcctggaa | 2160 |
| gtccctcgcc cacagtgtgt gttcacaccg actccacctc agagcatggt gccgtccgtt | 2220 |
| ttccccttcct agtgacccca ggtttagcat cgtcctatac tgttccctcc actcctccat | 2280 |
| gaccctctga gtgatgg | 2297 |

<210> SEQ ID NO 4
<211> LENGTH: 572
<212> TYPE: PRT
<213> ORGANISM: Mus musculus

<400> SEQUENCE: 4

-continued

```
Met Ser His Gln Gly Lys Lys Ser Ile Pro His Ile Thr Ser Asp Arg
1               5                   10                  15

Leu Leu Ile Arg Gly Arg Ile Ile Asn Asp Asp Gln Ser Phe Tyr
            20                  25                  30

Ala Asp Val Tyr Leu Glu Asp Gly Leu Ile Lys Gln Ile Gly Glu Asn
            35                  40                  45

Leu Ile Val Pro Gly Gly Val Lys Thr Ile Glu Ala Asn Gly Arg Met
50                      55                  60

Val Ile Pro Gly Gly Ile Asp Val Asn Thr Tyr Leu Gln Lys Pro Ser
65                  70                  75                  80

Gln Gly Met Thr Ser Ala Asp Asp Phe Phe Gln Gly Thr Lys Ala Ala
                85                  90                  95

Leu Ala Gly Gly Thr Thr Met Ile Ile Asp His Val Val Pro Glu Pro
            100                 105                 110

Gly Ser Ser Leu Leu Thr Ser Phe Glu Lys Trp His Glu Ala Ala Asp
            115                 120                 125

Thr Lys Ser Cys Cys Asp Tyr Ser Leu His Val Asp Ile Thr Ser Trp
130                 135                 140

Tyr Asp Gly Val Arg Glu Glu Leu Glu Val Leu Val Gln Asp Lys Gly
145                 150                 155                 160

Val Asn Ser Phe Gln Val Tyr Met Ala Tyr Lys Asp Leu Tyr Gln Met
                165                 170                 175

Ser Asp Ser Gln Leu Tyr Glu Ala Phe Thr Phe Leu Lys Gly Leu Gly
            180                 185                 190

Ala Val Ile Leu Val His Ala Glu Asn Gly Asp Leu Ile Ala Gln Glu
            195                 200                 205

Gln Lys Arg Ile Leu Glu Met Gly Ile Thr Gly Pro Glu Gly His Ala
210                 215                 220

Leu Ser Arg Pro Glu Glu Leu Glu Ala Glu Ala Val Phe Arg Ala Ile
225                 230                 235                 240

Ala Ile Ala Gly Arg Ile Asn Cys Pro Val Tyr Ile Thr Lys Val Met
                245                 250                 255

Ser Lys Ser Ala Ala Asp Ile Ile Ala Leu Ala Arg Lys Lys Gly Pro
            260                 265                 270

Leu Val Phe Gly Glu Pro Ile Ala Ala Ser Leu Gly Thr Asp Gly Thr
            275                 280                 285

His Tyr Trp Ser Lys Asn Trp Ala Lys Ala Ala Phe Val Thr Ser
290                 295                 300

Pro Pro Leu Ser Pro Asp Pro Thr Thr Pro Asp Tyr Leu Thr Ser Leu
305                 310                 315                 320

Leu Ala Cys Gly Asp Leu Gln Val Thr Gly Ser Gly His Cys Pro Tyr
                325                 330                 335

Ser Ile Ala Gln Lys Ala Val Gly Lys Asp Asn Phe Thr Leu Ile Pro
            340                 345                 350

Glu Gly Val Asn Gly Ile Glu Glu Arg Met Thr Val Val Trp Asp Lys
            355                 360                 365

Ala Val Ala Thr Gly Lys Met Asp Glu Asn Gln Phe Val Ala Val Thr
370                 375                 380

Ser Thr Asn Ala Ala Lys Ile Phe Asn Leu Tyr Pro Arg Lys Gly Arg
385                 390                 395                 400

Ile Ala Val Gly Ser Asp Ala Asp Val Val Ile Trp Asp Pro Asp Lys
                405                 410                 415
```

-continued

```
Met Lys Thr Ile Thr Ala Lys Ser His Lys Ser Thr Val Glu Tyr Asn
            420                 425                 430

Ile Phe Glu Gly Met Glu Cys His Gly Ser Pro Leu Val Val Ile Ser
            435                 440                 445

Gln Gly Lys Ile Val Phe Glu Asp Gly Asn Ile Ser Val Ser Lys Gly
            450                 455                 460

Met Gly Arg Phe Ile Pro Arg Lys Pro Phe Pro Glu His Leu Tyr Gln
465                 470                 475                 480

Arg Val Arg Ile Arg Ser Lys Val Phe Gly Leu His Ser Val Ser Arg
                485                 490                 495

Gly Met Tyr Asp Gly Pro Val Tyr Glu Val Pro Ala Thr Pro Lys His
                500                 505                 510

Ala Ala Pro Ala Pro Ser Ala Glu Ser Ser Pro Ser Lys His Gln Pro
            515                 520                 525

Pro Pro Ile Arg Asn Leu His Gln Ser Asn Phe Ser Leu Ser Gly Ala
            530                 535                 540

Gln Ile Asp Asp Asn Asn Pro Arg Arg Thr Gly His Arg Ile Val Ala
545                 550                 555                 560

Pro Pro Gly Gly Arg Ser Asn Ile Thr Ser Leu Gly
                565                 570
```

<210> SEQ ID NO 5
<211> LENGTH: 1920
<212> TYPE: DNA
<213> ORGANISM: Mus musculus

<400> SEQUENCE: 5

```
gctgactaat atgcttaaat tcagcgggtc gccacgtctg gtcggtacgt ccacgcccgc      60
gcagccccta ccgaggacac tcagcccgcc cgtgtatcag gatgtccttc caaggcaaga     120
agagcattcc ccggataacg agcgaccgcc ttctcatcaa aggtgggaag attgtgaacg     180
atgaccagtc ctttcatgct gatctgtatg tggaagacgg tctgattaaa caaattggag     240
aaaatctcat cgtccctggg ggcatcaaaa ccatcgatgc tcatggcctg atggtgctgc     300
ctgggggagt tgacgttcac acccggctgc agatgcctgt gatgggcatg accccagctg     360
atgatttctg tcaggcacc aaggcggctc tagcaggcgg gaccaccatg atattggacc      420
atgtgtttcc tgacgctggt gtgagcctgc tggcagccta tgagcagtgg cgggacggag     480
cagacagcgc ggcctgctgt gactactcct tacatgtgga cattcctcgc tggcacgaga     540
gcaccaaaga gagctggag gccctagtca gggacaaagg tgtgaactcc ttcctggtct      600
tcatggcata caaggacagg tgccagtgta ctgacggtca gatatatgaa atcttcagcc     660
tcatccggga cctgggagct gtggcccagg tgcacgcaga aaatgggac atcgtggagg      720
aggaacagaa gcgcctgctg gagcaaggca tcactggtcc tgagggccat gtgctcagcc     780
acccagaaga ggtagaggcc gaggctgtgt acagagcagt caccattgcc aagcaggcca     840
actgcccact atacgtcacc aaggtgatga gcaagggtgc agctgacatg gttgcccaag     900
ccaagcgcag gggggtggtc gtctttgggg aacctatcac tgccagcctg gcactgatg      960
gctcacacta ctggagcaag aactgggcca aggctgcagc ctttgtcact tcaccccta     1020
tcaacccgga ccctactact gcagaccacc tcacctctct gctgtccagt ggggacctcc    1080
aggtgacagg cagtgcccac tgcaccttca ctactgccca gaaggctgtt ggcaaagaca    1140
acttcacact gatccccgag gtagtcaacg gtatagaaga gcgcatgtct gtggtctggg    1200
agaaatgtgt ggcttcaggg aaaatggacg agaatgagtt cgttgccgtg accagcacaa    1260
```

-continued

```
atgctgccaa aatcttcaat ttttacccca ggaaggggcg tgtggccgtg ggctctgatg    1320
ctgacctggt catctggaac cccagggcca cgaaagtcat ctctgccaag agccataacc    1380
tgaatgtaga gtacaacatc tttgaaggag tggagtgccg aggagtgccc acggtggtca    1440
taagtcaggg cagagtggtg ctggaggacg gaaacctgct tgtcactcca ggggctggcc    1500
gcttcattcc ccggaagacg ttcccggact ttgtctataa gaggataaag gctcgcaaca    1560
ggctagcaga gatccacggt gtgcctcgag gcctgtacga cgggcctgtg catgaagtga    1620
tgttacctgc caagccagga agtggcacac aggcccgtgc atcctgttca ggcaagatct    1680
cagtgccacc cgtgcgcaac ctgcaccagt cggggttcag cctatctggc tctcaggctg    1740
acgatcacat tgccagacgt acggctcaga agatcatggc accccccgga ggacgctcca    1800
acatcacgtc tctttcctag acttggggtc ttggcaagct ggtgctgtcc ccactggcag    1860
ggtgtgggga cgactcacgt cagttagctc cttcctttgt agattgttat tgtgaaaggc    1920
```

<210> SEQ ID NO 6
<211> LENGTH: 572
<212> TYPE: PRT
<213> ORGANISM: Mus musculus

<400> SEQUENCE: 6

```
Met Ser Phe Gln Gly Lys Lys Ser Ile Pro Arg Ile Thr Ser Asp Arg
1               5                   10                  15

Leu Leu Ile Lys Gly Gly Lys Ile Val Asn Asp Asp Gln Ser Phe His
            20                  25                  30

Ala Asp Leu Tyr Val Glu Asp Gly Leu Ile Lys Gln Ile Gly Glu Asn
        35                  40                  45

Leu Ile Val Pro Gly Gly Ile Lys Thr Ile Asp Ala His Gly Leu Met
    50                  55                  60

Val Leu Pro Gly Gly Val Asp Val His Thr Arg Leu Gln Met Pro Val
65                  70                  75                  80

Met Gly Met Thr Pro Ala Asp Asp Phe Cys Gln Gly Thr Lys Ala Ala
                85                  90                  95

Leu Ala Gly Gly Thr Thr Met Ile Leu Asp His Val Phe Pro Asp Ala
            100                 105                 110

Gly Val Ser Leu Leu Ala Ala Tyr Glu Gln Trp Arg Asp Gly Ala Asp
        115                 120                 125

Ser Ala Ala Cys Cys Asp Tyr Ser Leu His Val Asp Ile Pro Arg Trp
    130                 135                 140

His Glu Ser Thr Lys Glu Glu Leu Glu Ala Leu Val Arg Asp Lys Gly
145                 150                 155                 160

Val Asn Ser Phe Leu Val Phe Met Ala Tyr Lys Asp Arg Cys Gln Cys
                165                 170                 175

Thr Asp Gly Gln Ile Tyr Glu Ile Phe Ser Leu Ile Arg Asp Leu Gly
            180                 185                 190

Ala Val Ala Gln Val His Ala Glu Asn Gly Asp Ile Val Glu Glu Glu
        195                 200                 205

Gln Lys Arg Leu Leu Glu Gln Gly Ile Thr Gly Pro Glu Gly His Val
    210                 215                 220

Leu Ser His Pro Glu Glu Val Glu Ala Glu Val Tyr Arg Ala Val
225                 230                 235                 240

Thr Ile Ala Lys Gln Ala Asn Cys Pro Leu Tyr Val Thr Lys Val Met
                245                 250                 255
```

```
Ser Lys Gly Ala Ala Asp Met Val Ala Gln Ala Lys Arg Arg Gly Val
            260                 265                 270

Val Val Phe Gly Glu Pro Ile Thr Ala Ser Leu Gly Thr Asp Gly Ser
        275                 280                 285

His Tyr Trp Ser Lys Asn Trp Ala Lys Ala Ala Phe Val Thr Ser
    290                 295                 300

Pro Pro Ile Asn Pro Asp Pro Thr Thr Ala Asp His Leu Thr Ser Leu
305                 310                 315                 320

Leu Ser Ser Gly Asp Leu Gln Val Thr Gly Ser Ala His Cys Thr Phe
                325                 330                 335

Thr Thr Ala Gln Lys Ala Val Gly Lys Asp Asn Phe Thr Leu Ile Pro
            340                 345                 350

Glu Val Val Asn Gly Ile Glu Glu Arg Met Ser Val Val Trp Glu Lys
        355                 360                 365

Cys Val Ala Ser Gly Lys Met Asp Glu Asn Glu Phe Val Ala Val Thr
    370                 375                 380

Ser Thr Asn Ala Ala Lys Ile Phe Asn Phe Tyr Pro Arg Lys Gly Arg
385                 390                 395                 400

Val Ala Val Gly Ser Asp Ala Asp Leu Val Ile Trp Asn Pro Arg Ala
                405                 410                 415

Thr Lys Val Ile Ser Ala Lys Ser His Asn Leu Asn Val Glu Tyr Asn
            420                 425                 430

Ile Phe Glu Gly Val Glu Cys Arg Gly Val Pro Thr Val Val Ile Ser
        435                 440                 445

Gln Gly Arg Val Val Leu Glu Asp Gly Asn Leu Leu Val Thr Pro Gly
    450                 455                 460

Ala Gly Arg Phe Ile Pro Arg Lys Thr Phe Pro Asp Phe Val Tyr Lys
465                 470                 475                 480

Arg Ile Lys Ala Arg Asn Arg Leu Ala Glu Ile His Gly Val Pro Arg
                485                 490                 495

Gly Leu Tyr Asp Gly Pro Val His Glu Val Met Leu Pro Ala Lys Pro
            500                 505                 510

Gly Ser Gly Thr Gln Ala Arg Ala Ser Cys Ser Gly Lys Ile Ser Val
        515                 520                 525

Pro Pro Val Arg Asn Leu His Gln Ser Gly Phe Ser Leu Ser Gly Ser
530                 535                 540

Gln Ala Asp Asp His Ile Ala Arg Arg Thr Ala Gln Lys Ile Met Ala
545                 550                 555                 560

Pro Pro Gly Gly Arg Ser Asn Ile Thr Ser Leu Ser
                565                 570

<210> SEQ ID NO 7
<211> LENGTH: 1690
<212> TYPE: DNA
<213> ORGANISM: Homo sapiens

<400> SEQUENCE: 7 gccgcccta ccagagaccc ccaggagcag gatgtccttc cagggcaaga aaagcatccc     60
ccggatcacg agtgaccgcc ttctgatcag aggtgggagg atcgtgaatg acgaccagtc    120
cttttacgct gatgtgcacg tggaagatgc cttgataaaa caaatcggag aaaacctcat    180
cgtccctggg ggcatcaaga ccattgacgc ccacggcctg atggtccttc ctggtggcgt    240
tgacgtccac acaaggctgc agatgcctgt cctgggcatg acaccggctg acgacttctg    300
tcagggcacc aaggcagcgc tagcaggagg aaccaccatg atcttggacc acgtcttccc    360
```

```
cgacacgggt gtgagcctgc tggcggccta cgagcagtgg cgggagcggg cggacagcgc    420
ggcctgctgc gactactccc tgcacgtgga catcacccga tggcatgaga gcatcaagga    480
ggagctggag gccctggtca aggagaaggg tgtgaactcc ttcctggtct tcatggcata    540
caaggaccgg tgccagtgca gcgacagcca gatgtacgag atcttcagca tcatccggga    600
cctgggggcc ttggcccagg tgcacgctga aacggggac atcgtggagg aggagcagaa     660
gcggttgctg gagctcggca tcactggccc cgagggccac gtgctcagcc accccgagga    720
ggtggaggct gaggcggtgt accgagctgt caccatcgcc aagcaggcaa actgcccgct    780
gtacgtcacc aaggtgatga gcaaggggc ggccgacgcc atcgctcagg ccaagcgcag     840
aggggtggtc gtgtttgggg agcccatcac cgccagcctg gcaccgacg gttcacacta     900 ctggagcaag aactgggcca aggctgcagc cttcgtcaca tcaccccctg tcaacccaga    960
ccccaccacg gcagaccacc tcacctgctt gctgtccagc ggggacctcc aggtgacagg    1020
cagcgcccac tgcaccttca ccactgccca gaaggctgtg gcaaggaca acttcgcgct    1080 gatccccgag ggcaccaacg gcattgagga gcgcatgtcg atggtctggg agaaatgtgt    1140
ggcctctggg aagatggacg agaatgagtt cgtcgcggtg accagtacaa atgctgccaa    1200
aatcttcaat ttttacccaa ggaaggggcg agtggctgtg ggctctgacg ctgacctggt    1260
catatggaac cccaaggcca ccaagatcat ctctgccaag acccacaatc tgaacgtgga    1320
gtacaacatc ttcgagggag tggagtgccg gggagcgcct gccgtggtca taagtcaggg    1380
ccgagtggcg ctggaggacg ggaagatgtt tgtcaccccg ggggcgggcc gcttcgtccc    1440
tcggaaaaca ttcccggact ttgtctacaa gaggatcaaa gctcgcaaca ggctggcgga    1500
gatccacggt gtgccccgtg ggctgtatga cgggcccgtc cacgaggtga tggtgcctgc    1560
caagccaggg agtggcgctc cggccgcgc gtcctgccca ggcaagatct ccgtgcctcc     1620
tgtgcgcaac ctacatcagt cggggttcag cctatctggg tctcaggctg atgaccacat    1680
cgcccgacgc                                                            1690
```

<210> SEQ ID NO 8
<211> LENGTH: 572
<212> TYPE: PRT
<213> ORGANISM: Homo sapiens

<400> SEQUENCE: 8

```
Met Ser Phe Gln Gly Lys Lys Ser Ile Pro Arg Ile Thr Ser Asp Arg
1               5                   10                  15

Leu Leu Ile Arg Gly Gly Arg Ile Val Asn Asp Asp Gln Ser Phe Tyr
            20                  25                  30

Ala Asp Val His Val Glu Asp Gly Leu Ile Lys Gln Ile Gly Glu Asn
        35                  40                  45

Leu Ile Val Pro Gly Gly Ile Lys Thr Ile Asp Ala His Gly Leu Met
    50                  55                  60

Val Leu Pro Gly Gly Val Asp Val His Thr Arg Leu Gln Met Pro Val
65                  70                  75                  80

Leu Gly Met Thr Pro Ala Asp Asp Phe Cys Gln Gly Thr Lys Ala Ala
                85                  90                  95

Leu Ala Gly Gly Thr Thr Met Ile Leu Asp His Val Phe Pro Asp Thr
            100                 105                 110

Gly Val Ser Leu Leu Ala Ala Tyr Glu Gln Trp Arg Glu Arg Ala Asp
        115                 120                 125
```

-continued

```
Ser Ala Ala Cys Cys Asp Tyr Ser Leu His Val Asp Ile Thr Arg Trp
    130                 135                 140

His Glu Ser Ile Lys Glu Glu Leu Glu Ala Leu Val Lys Glu Lys Gly
145                 150                 155                 160

Val Asn Ser Phe Leu Val Phe Met Ala Tyr Lys Asp Arg Cys Gln Cys
                165                 170                 175

Ser Asp Ser Gln Met Tyr Glu Ile Phe Ser Ile Ile Arg Asp Leu Gly
                180                 185                 190

Ala Leu Ala Gln Val His Ala Glu Asn Gly Asp Ile Val Glu Glu Glu
            195                 200                 205

Gln Lys Arg Leu Leu Glu Leu Gly Ile Thr Gly Pro Glu Gly His Val
    210                 215                 220

Leu Ser His Pro Glu Glu Val Glu Ala Glu Ala Val Tyr Arg Ala Val
225                 230                 235                 240

Thr Ile Ala Lys Gln Ala Asn Cys Pro Leu Tyr Val Thr Lys Val Met
                245                 250                 255

Ser Lys Gly Ala Ala Asp Ala Ile Ala Gln Ala Lys Arg Arg Gly Val
                260                 265                 270

Val Val Phe Gly Glu Pro Ile Thr Ala Ser Leu Gly Thr Asp Gly Ser
            275                 280                 285

His Tyr Trp Ser Lys Asn Trp Ala Lys Ala Ala Ala Phe Val Thr Ser
    290                 295                 300

Pro Pro Val Asn Pro Asp Pro Thr Thr Ala Asp His Leu Thr Cys Leu
305                 310                 315                 320

Leu Ser Ser Gly Asp Leu Gln Val Thr Gly Ser Ala His Cys Thr Phe
                325                 330                 335

Thr Thr Ala Gln Lys Ala Val Gly Lys Asp Asn Phe Ala Leu Ile Pro
                340                 345                 350

Glu Gly Thr Asn Gly Ile Glu Glu Arg Met Ser Met Val Trp Glu Lys
            355                 360                 365

Cys Val Ala Ser Gly Lys Met Asp Glu Asn Glu Phe Val Ala Val Thr
    370                 375                 380

Ser Thr Asn Ala Ala Lys Ile Phe Asn Phe Tyr Pro Arg Lys Gly Arg
385                 390                 395                 400

Val Ala Val Gly Ser Asp Ala Asp Leu Val Ile Trp Asn Pro Lys Ala
                405                 410                 415

Thr Lys Ile Ile Ser Ala Lys Thr His Asn Leu Asn Val Glu Tyr Asn
                420                 425                 430

Ile Phe Glu Gly Val Glu Cys Arg Gly Ala Pro Ala Val Val Ile Ser
            435                 440                 445

Gln Gly Arg Val Ala Leu Glu Asp Gly Lys Met Phe Val Thr Pro Gly
    450                 455                 460

Ala Gly Arg Phe Val Pro Arg Lys Thr Phe Pro Asp Phe Val Tyr Lys
465                 470                 475                 480

Arg Ile Lys Ala Arg Asn Arg Leu Ala Glu Ile His Gly Val Pro Arg
                485                 490                 495

Gly Leu Tyr Asp Gly Pro Val His Glu Val Met Val Pro Ala Lys Pro
                500                 505                 510

Gly Ser Gly Ala Pro Ala Arg Ala Ser Cys Pro Gly Lys Ile Ser Val
            515                 520                 525

Pro Pro Val Arg Asn Leu His Gln Ser Gly Phe Ser Leu Ser Gly Ser
    530                 535                 540

Gln Ala Asp Asp His Ile Ala Arg Arg Thr Ala Gln Lys Ile Met Ala
```

```
                    545                 550                 555                 560
Pro Pro Gly Gly Arg Ser Asn Ile Thr Ser Leu Ser
                565                 570

<210> SEQ ID NO 9
<211> LENGTH: 55
<212> TYPE: PRT
<213> ORGANISM: Homo sapiens
<220> FEATURE:
<221> NAME/KEY: MISC_FEATURE
<222> LOCATION: (1)..(55)
<223> OTHER INFORMATION: amino acids 1 to 55 of the sequence shown in
      Figure 12

<400> SEQUENCE: 9

Met Ser Phe Gln Gly Lys Lys Ser Ile Pro Arg Ile Thr Ser Asp Arg
1               5                   10                  15

Leu Leu Ile Arg Gly Gly Arg Ile Val Asn Asp Asp Gln Ser Phe Tyr
            20                  25                  30

Ala Asp Val His Val Glu Asp Gly Leu Ile Lys Gln Ile Gly Glu Asn
        35                  40                  45

Leu Ile Val Pro Gly Gly Ile
    50                  55

<210> SEQ ID NO 10
<211> LENGTH: 497
<212> TYPE: PRT
<213> ORGANISM: Homo sapiens
<220> FEATURE:
<221> NAME/KEY: MISC_FEATURE
<222> LOCATION: (1)..(516)
<223> OTHER INFORMATION: amino acids 57 to 553 of the sequence shown in
      Figure 12

<400> SEQUENCE: 10

Thr Ile Asp Ala His Gly Leu Met Val Leu Pro Gly Gly Val Asp Val
1               5                   10                  15

His Thr Arg Leu Gln Met Pro Val Leu Gly Met Thr Pro Ala Asp Asp
            20                  25                  30

Phe Cys Gln Gly Thr Lys Ala Ala Leu Ala Gly Gly Thr Thr Met Ile
        35                  40                  45

Leu Asp His Val Phe Pro Asp Thr Gly Val Ser Leu Leu Ala Ala Tyr
    50                  55                  60

Glu Gln Trp Arg Glu Arg Ala Asp Ser Ala Ala Cys Cys Asp Tyr Ser
65              70                  75                  80

Leu His Val Asp Ile Thr Arg Trp His Glu Ser Ile Lys Glu Glu Leu
            85                  90                  95

Glu Ala Leu Val Lys Glu Lys Gly Val Asn Ser Phe Leu Val Phe Met
            100                 105                 110

Ala Tyr Lys Asp Arg Cys Gln Cys Ser Asp Ser Gln Met Tyr Glu Ile
        115                 120                 125

Phe Ser Ile Ile Arg Asp Leu Gly Ala Leu Ala Gln Val His Ala Glu
130                 135                 140

Asn Gly Asp Ile Val Glu Glu Glu Gln Lys Arg Leu Leu Glu Leu Gly
145                 150                 155                 160

Ile Thr Gly Pro Glu Gly His Val Leu Ser His Pro Glu Glu Val Glu
            165                 170                 175

Ala Glu Ala Val Tyr Arg Ala Val Thr Ile Ala Lys Gln Ala Asn Cys
            180                 185                 190
```

-continued

```
Pro Leu Tyr Val Thr Lys Val Met Ser Lys Gly Ala Ala Asp Ala Ile
            195                 200                 205

Ala Gln Ala Lys Arg Arg Gly Val Val Phe Gly Glu Pro Ile Thr
    210                 215                 220

Ala Ser Leu Gly Thr Asp Gly Ser His Tyr Trp Ser Lys Asn Trp Ala
225                 230                 235                 240

Lys Ala Ala Ala Phe Val Thr Ser Pro Val Asn Pro Asp Pro Thr
                245                 250                 255

Thr Ala Asp His Leu Thr Cys Leu Leu Ser Ser Gly Asp Leu Gln Val
                260                 265                 270

Thr Gly Ser Ala His Cys Thr Phe Thr Thr Ala Gln Lys Ala Val Gly
            275                 280                 285

Lys Asp Asn Phe Ala Leu Ile Pro Glu Gly Thr Asn Gly Ile Glu Glu
    290                 295                 300

Arg Met Ser Met Val Trp Glu Lys Cys Val Ala Ser Gly Lys Met Asp
305                 310                 315                 320

Glu Asn Glu Phe Val Ala Val Thr Ser Thr Asn Ala Ala Lys Ile Phe
                325                 330                 335

Asn Phe Tyr Pro Arg Lys Gly Arg Val Ala Val Gly Ser Asp Ala Asp
                340                 345                 350

Leu Val Ile Trp Asn Pro Lys Ala Thr Lys Ile Ile Ser Ala Lys Thr
            355                 360                 365

His Asn Leu Asn Val Glu Tyr Asn Ile Phe Glu Gly Val Glu Cys Arg
370                 375                 380

Gly Ala Pro Ala Val Val Ile Ser Gln Gly Arg Val Ala Leu Glu Asp
385                 390                 395                 400

Gly Lys Met Phe Val Thr Pro Gly Ala Gly Arg Phe Val Pro Arg Lys
                405                 410                 415

Thr Phe Pro Asp Phe Val Tyr Lys Arg Ile Lys Ala Arg Asn Arg Leu
                420                 425                 430

Ala Glu Ile His Gly Val Pro Arg Gly Leu Tyr Asp Gly Pro Val His
            435                 440                 445

Glu Val Met Val Pro Ala Lys Pro Gly Ser Gly Ala Pro Ala Arg Ala
    450                 455                 460

Ser Cys Pro Gly Lys Ile Ser Val Pro Pro Val Arg Asn Leu His Gln
465                 470                 475                 480

Ser Gly Phe Ser Leu Ser Gly Ser Gln Ala Asp Asp His Ile Ala Arg
                485                 490                 495

Arg

<210> SEQ ID NO 11
<211> LENGTH: 6
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa corresponds to a non-determined amino acid

<400> SEQUENCE: 11

Xaa Met Tyr Asp Gly Pro
1               5

<210> SEQ ID NO 12
<211> LENGTH: 7
<212> TYPE: PRT
<213> ORGANISM: Mus musculus
```

-continued

```
<220> FEATURE:
<221> NAME/KEY: MISC_FEATURE
<222> LOCATION: (1)..(1)
<223> OTHER INFORMATION: Xaa corresponds to a non-determined amino acid

<400> SEQUENCE: 12

Xaa Phe Asn Leu Tyr Pro Arg
1               5

<210> SEQ ID NO 13
<211> LENGTH: 13
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa corresponds to a non-determined amino acid

<400> SEQUENCE: 13

Xaa Val Leu Glu Asp Gly Thr Leu His Val Thr Glu Gly
1               5                   10

<210> SEQ ID NO 14
<211> LENGTH: 20
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa corresponds to a non-determined amino acid
<220> FEATURE:
<221> NAME/KEY: MISC_FEATURE
<222> LOCATION: (4)..(5)
<223> OTHER INFORMATION: Xaa corresponds to a non-determined amino acid
<220> FEATURE:
<221> NAME/KEY: MISC_FEATURE
<222> LOCATION: (9)..(9)
<223> OTHER INFORMATION: Xaa corresponds to a probable but uncertain His
      residue
<220> FEATURE:
<221> NAME/KEY: MISC_FEATURE
<222> LOCATION: (14)..(14)
<223> OTHER INFORMATION: Xaa corresponds to a non-determined amino acid

<400> SEQUENCE: 14

Xaa Ile Gly Xaa Xaa Ala Gln Val Xaa Ala Glu Asn Gly Xaa Ile Ile
1               5                   10                  15

Ala Glu Glu Gln
            20

<210> SEQ ID NO 15
<211> LENGTH: 10
<212> TYPE: PRT
<213> ORGANISM: Mus musculus
<220> FEATURE:
<221> NAME/KEY: MISC_FEATURE
<222> LOCATION: (1)..(2)
<223> OTHER INFORMATION: Xaa corresponds to a non-determined amino acid

<400> SEQUENCE: 15

Xaa Xaa Glu Asn Gln Phe Val Ala Val Thr
1               5                   10

<210> SEQ ID NO 16
<211> LENGTH: 19
<212> TYPE: PRT
<213> ORGANISM: Mus musculus
<220> FEATURE:
<221> NAME/KEY: MISC_FEATURE
<222> LOCATION: (1)..(1)
```

```
<223> OTHER INFORMATION: Xaa corrsponds to a non-determined amino acid
<220> FEATURE:
<221> NAME/KEY: MISC_FEATURE
<222> LOCATION: (5)..(5)
<223> OTHER INFORMATION: Xaa corrsponds to a probably but non-determined
      Asp amino acid residue
<220> FEATURE:
<221> NAME/KEY: MISC_FEATURE
<222> LOCATION: (16)..(16)
<223> OTHER INFORMATION: Xaa corrsponds to a probably but non-determined
      Asp amino acid residue
<220> FEATURE:
<221> NAME/KEY: MISC_FEATURE
<222> LOCATION: (17)..(17)
<223> OTHER INFORMATION: Xaa corrsponds to a probably but non-determined
      Gly amino acid residue

<400> SEQUENCE: 16

Xaa Val Asn Asp Xaa Gln Ser Phe Tyr Ala Asp Ile Tyr Met Glu Xaa
1               5                   10                  15

Xaa Leu Ile

<210> SEQ ID NO 17
<211> LENGTH: 12
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: Xaa corresponds to a non-determined amino acid
<220> FEATURE:
<221> NAME/KEY: MISC_FEATURE
<222> LOCATION: (7)..(7)
<223> OTHER INFORMATION: Xaa corresponds to a non-determined amino acid
<220> FEATURE:
<221> NAME/KEY: MISC_FEATURE
<222> LOCATION: (9)..(9)
<223> OTHER INFORMATION: Xaa corresponds to a non-determined amino acid
<220> FEATURE:
<221> NAME/KEY: MISC_FEATURE
<222> LOCATION: (11)..(11)
<223> OTHER INFORMATION: Xaa corresponds to a non-determined amino acid

<400> SEQUENCE: 17

Xaa Xaa Xaa Phe Val Thr Xaa Pro Xaa Leu Xaa Pro
1               5                   10

<210> SEQ ID NO 18
<211> LENGTH: 6
<212> TYPE: PRT
<213> ORGANISM: Mus musculus

<400> SEQUENCE: 18

Ile Ile Ala Glu Glu Gln
1               5

<210> SEQ ID NO 19
<211> LENGTH: 8
<212> TYPE: PRT
<213> ORGANISM: Mus musculus
<220> FEATURE:
<221> NAME/KEY: MISC_FEATURE
<222> LOCATION: (8)..(8)
<223> OTHER INFORMATION: Xaa corresponds to a probably but uncertain Asp
      amino acid residue

<400> SEQUENCE: 19

Tyr Ala Asp Ile Tyr Met Glu Xaa
1               5
```

```
<210> SEQ ID NO 20
<211> LENGTH: 14
<212> TYPE: DNA
<213> ORGANISM: Artificial
<220> FEATURE:
<223> OTHER INFORMATION: oligonucleotide probe sequence
<220> FEATURE:
<221> NAME/KEY: misc_feature
<222> LOCATION: (3)..(3)
<223> OTHER INFORMATION: n corresponds to either C or T
<220> FEATURE:
<221> NAME/KEY: misc_feature
<222> LOCATION: (9)..(9)
<223> OTHER INFORMATION: n corresponds to either T or A
<220> FEATURE:
<221> NAME/KEY: misc_feature
<222> LOCATION: (12)..(12)
<223> OTHER INFORMATION: n corresponds to either A or G

<400> SEQUENCE: 20
atnattgcng anca                                                    14

<210> SEQ ID NO 21
<211> LENGTH: 16
<212> TYPE: DNA
<213> ORGANISM: Artificial
<220> FEATURE:
<223> OTHER INFORMATION: oligonucleotide probe
<220> FEATURE:
<221> NAME/KEY: misc_feature
<222> LOCATION: (3)..(3)
<223> OTHER INFORMATION: n corresponds to either C or T
<220> FEATURE:
<221> NAME/KEY: misc_feature
<222> LOCATION: (6)..(6)
<223> OTHER INFORMATION: n corresponds to either T or C
<220> FEATURE:
<221> NAME/KEY: misc_feature
<222> LOCATION: (9)..(9)
<223> OTHER INFORMATION: n corresponds to either T or A
<220> FEATURE:
<221> NAME/KEY: misc_feature
<222> LOCATION: (14)..(14)
<223> OTHER INFORMATION: n corresponds to either A or G

<400> SEQUENCE: 21
tgntcnacng catnat                                                  16

<210> SEQ ID NO 22
<211> LENGTH: 17
<212> TYPE: DNA
<213> ORGANISM: Artificial
<220> FEATURE:
<223> OTHER INFORMATION: oligonucleotide probe
<220> FEATURE:
<221> NAME/KEY: misc_feature
<222> LOCATION: (6)..(6)
<223> OTHER INFORMATION: n corresponds to either A or T
<220> FEATURE:
<221> NAME/KEY: misc_feature
<222> LOCATION: (9)..(9)
<223> OTHER INFORMATION: n corresponds to either C or T
<220> FEATURE:
<221> NAME/KEY: misc_feature
<222> LOCATION: (12)..(12)
<223> OTHER INFORMATION: n corresponds to either C or T

<400> SEQUENCE: 22
tatgcngana tnatgga                                                 17

<210> SEQ ID NO 23
<211> LENGTH: 17
<212> TYPE: DNA
```

```
<213> ORGANISM: Artificial
<220> FEATURE:
<223> OTHER INFORMATION: oligonucleotide probe
<220> FEATURE:
<221> NAME/KEY: misc_feature
<222> LOCATION: (6)..(6)
<223> OTHER INFORMATION: n corresponds to either G or A
<220> FEATURE:
<221> NAME/KEY: misc_feature
<222> LOCATION: (9)..(9)
<223> OTHER INFORMATION: n corresponds to either G or A
<220> FEATURE:
<221> NAME/KEY: misc_feature
<222> LOCATION: (12)..(12)
<223> OTHER INFORMATION: n corresponds to either T or A

<400> SEQUENCE: 23
tccatntanc tngcata                                                     17

<210> SEQ ID NO 24
<211> LENGTH: 23
<212> TYPE: DNA
<213> ORGANISM: Artificial
<220> FEATURE:
<223> OTHER INFORMATION: primer sequence

<400> SEQUENCE: 24
ggcatatgtc ttatcagggg aag                                              23

<210> SEQ ID NO 25
<211> LENGTH: 24
<212> TYPE: DNA
<213> ORGANISM: Artificial
<220> FEATURE:
<223> OTHER INFORMATION: primer sequence

<400> SEQUENCE: 25
gcgaattctt agcccaggct gatg                                             24

<210> SEQ ID NO 26
<211> LENGTH: 12
<212> TYPE: PRT
<213> ORGANISM: Artificial
<220> FEATURE:
<223> OTHER INFORMATION: artificial peptide antigen

<400> SEQUENCE: 26

Leu Glu Asp Gly Thr Leu His Val Thr Glu Gly Ser
1               5                   10

<210> SEQ ID NO 27
<211> LENGTH: 28
<212> TYPE: DNA
<213> ORGANISM: Artificial
<220> FEATURE:
<223> OTHER INFORMATION: polynucleotide sequence
<220> FEATURE:
<221> NAME/KEY: misc_feature
<222> LOCATION: (1)..(28)
<223> OTHER INFORMATION: polynucleotide sequence between restrictions
      sites EcoRI and BamHI

<400> SEQUENCE: 27
atggactaca aggacgacga tgacaagg                                         28

<210> SEQ ID NO 28
<211> LENGTH: 18
<212> TYPE: DNA
<213> ORGANISM: Artificial
```

```
<220> FEATURE:
<223> OTHER INFORMATION: oligonucleotide probe

<400> SEQUENCE: 28
atagaggagc ggatgacg                                                    18

<210> SEQ ID NO 29
<211> LENGTH: 25
<212> TYPE: DNA
<213> ORGANISM: Artificial
<220> FEATURE:
<223> OTHER INFORMATION: oligonucleotide probe

<400> SEQUENCE: 29
gctgttatgg tcttcaactt gtcgg                                            25

<210> SEQ ID NO 30
<211> LENGTH: 26
<212> TYPE: DNA
<213> ORGANISM: Artificial
<220> FEATURE:
<223> OTHER INFORMATION: oligonucleotide probe

<400> SEQUENCE: 30
ggcctgttat ggtcttcaac ttgtcg                                           26

<210> SEQ ID NO 31
<211> LENGTH: 20
<212> TYPE: DNA
<213> ORGANISM: Artificial
<220> FEATURE:
<223> OTHER INFORMATION: oligonucleotide probe

<400> SEQUENCE: 31
aggaggagtg aagaccatcg                                                  20

<210> SEQ ID NO 32
<211> LENGTH: 22
<212> TYPE: DNA
<213> ORGANISM: Artificial
<220> FEATURE:
<223> OTHER INFORMATION: oligonucleotide probe

<400> SEQUENCE: 32
cttatgccac tcgctgatgt cc                                               22

<210> SEQ ID NO 33
<211> LENGTH: 19
<212> TYPE: DNA
<213> ORGANISM: Artificial
<220> FEATURE:
<223> OTHER INFORMATION: primer sequence

<400> SEQUENCE: 33
catctggctg tcgctgcac                                                   19

<210> SEQ ID NO 34
<211> LENGTH: 19
<212> TYPE: DNA
<213> ORGANISM: Artificial
<220> FEATURE:
<223> OTHER INFORMATION: primer sequence

<400> SEQUENCE: 34 gccgcccta ccagagacc                                                    19
```

```
<210> SEQ ID NO 35
<211> LENGTH: 18
<212> TYPE: DNA
<213> ORGANISM: Artificial
<220> FEATURE:
<223> OTHER INFORMATION: primer sequence

<400> SEQUENCE: 35
ggagattcag tgtggtgg                                                  18

<210> SEQ ID NO 36
<211> LENGTH: 20
<212> TYPE: DNA
<213> ORGANISM: Artificial
<220> FEATURE:
<223> OTHER INFORMATION: primer sequence

<400> SEQUENCE: 36
ggctctccag aacatcatcc                                                20

<210> SEQ ID NO 37
<211> LENGTH: 11
<212> TYPE: PRT
<213> ORGANISM: Artificial
<220> FEATURE:
<223> OTHER INFORMATION: artifical peptide sequence

<400> SEQUENCE: 37

Gly Ser Ala Arg Gly Ser Pro Thr Arg Pro Asn
1               5                   10

<210> SEQ ID NO 38
<211> LENGTH: 12
<212> TYPE: PRT
<213> ORGANISM: Artificial
<220> FEATURE:
<223> OTHER INFORMATION: artificial peptide sequence

<400> SEQUENCE: 38

Ser Ser Ala Lys Thr Ser Pro Ala Lys Gln Gln Ala
1               5                   10

<210> SEQ ID NO 39
<211> LENGTH: 11
<212> TYPE: PRT
<213> ORGANISM: Artificial
<220> FEATURE:
<223> OTHER INFORMATION: artificial peptide sequence

<400> SEQUENCE: 39

Pro Ser Ala Lys Ser Ser Pro Ser Lys His Gln
1               5                   10

<210> SEQ ID NO 40
<211> LENGTH: 11
<212> TYPE: PRT
<213> ORGANISM: Artificial
<220> FEATURE:
<223> OTHER INFORMATION: artificial peptide sequence

<400> SEQUENCE: 40

Pro Ala Arg Ala Ser Cys Pro Gly Lys Ile Ser
1               5                   10
```

USE OF ULIP PROTEINS IN THE DIAGNOSIS AND THERAPY OF CANCERS AND PARANEOPLASTIC NEUROLOGICAL SYNDROMES

This is a 371 of PCT/FR98/00328 filed Feb. 19, 1998.

FIELD OF THE INVENTION

The invention relates to the use of proteins designed ULIP/POP in the diagnosis and therapy of cancers and paraneoplastic neurological syndromes.

BACKGROUND OF THE INVENTION

Paraneoplastic neurological syndromes (PNS) occur in the instance of a cancer, often before its discovery, and are not connected either to the tumour proliferation itself (direct invasion, metastases) or to the therapy. Their frequency is globally estimated at approximately 1% of cancers. Several clinical pictures have been individualized for a long time (encephalomyelitis, Denny-Brown's sensitive neuropathy, cerebellar atrophy, limbic encephalitis, opsoclonus, . . . ) corresponding in fact to the either elective or preferential attack of certain groups of neurons. The frequency of inflammatory cells in the neighbourhood of the lesions for numerous years brought to mind the possibility of an auto-immune or viral process. The more recent demonstration of auto-antibodies in the serum and the cerebrospinal fluid (CSF) of patients suffering from PNS, specific to the type of tumour and the type of neurons which degenerate, has revived the hypothesis of participation of auto-immunity in the genesis of this pathology (Graus et al., 1985; Greenlee et al., 1983).

Apart from the presence of a high titre of these antibodies in the blood and the CSF of patients, there are several arguments suggesting that PNS depend on auto-immune mechanisms. Thus the antigens recognized in the central nervous system are also present in the tumours of patients (Anderson et al., 1987). At the level of the tumour tissue, antibodies specifically directed against these antigens as well as B and T lymphocytes are found (Hetzel et al., 1990).

These data suggest that the auto-immune process could be triggered by the expression of tumour antigens. A cross-immunity process could provoke the lesions of the central nervous system. Other arguments additionally indicate that the cerebral lesions result from the auto-immune response. Thus, in the brain of the patients, the titre of specific antibodies is higher than that of the serum and the CSF (Dalmau et al., 1991). In addition, in the case of encephalomyelitis associated with anti-Hu antibodies, there is an intense lymphocytic reaction, made up of B and T cells, situated in proximity to neurons in the process of destruction (Dalmau et al., 1991; Graus et al., 1990).

Several types of auto-antibodies allowing precise syndromic groupings as a function of immunological, neurological and carcinogenic criteria have been described.

Thus, anti-Yo antibodies are found in the serum and the CSF of women having paraneoplastic cerebellar atrophy and a gynaecological cancer (ovary, breast or uterus) (Greenlee et al., 1983; Jaeckle et al., 1985).

These antibodies recognize two cytoplasmic proteins of 34 and 62 kDa specific to Purkinje cells of the cerebellum.

The anti-Ri antibodies are found in the serum and the CSF of patients (principally of women) having opso-myoclonus, cerebellar syndrome and breast cancer. These antibodies recognize two proteins of 50 and 80 kDa specific to neurons of the central nervous system (Luque et al., 1991).

Anti-Hu antibodies are most frequently found in the course of PNS. They are found in the serum and the CSF of patients having Denny-Brown's syndrome or encephalomyeloneuritis and small-cell lung cancer (Graus et al., 1985; Dalmau et al., 1992). These auto-antibodies recognize several proteins of 37 to 45 kDa expressed specifically by all the neurons of the nervous system.

Another type of auto-antibody has recently been identified in patients having PNS: anti-CV2 antibodies (Antoine et al., 1993; Honnorat et al., 1996). The latter are atypical, in the sense that the antigenic target recognized in adulthood is essentially non-neuronal, although the post-mortem analysis of the brain of four patients allows neuronal loss, gliosis and an inflammatory process characteristic of PNS to be objectivized.

The originality of the discovery of these auto-antibodies resides, on the one hand, in their demonstration. The latter escaped all the usual investigations which consisted in revealing the antigens recognized by immunohistochemistry on post-mortem brain. The antigen recognized is indeed soluble and disappears from post-mortem brain under the majority of fixation conditions. Only fixation of human post-mortem tissue by immersion in paraformaldehyde or in situ by perfusion of paraformaldehyde in animals has allowed the presence of these antibodies in the CSF or the serum of patients suffering from PNS to be revealed (Antoine et al., 1993; Honnorat et al., 1996).

The anti-CV2 auto-antibodies present in the sera of patients suffering from paraneoplastic neurological syndrome (PNS) have been defined by their capacity to recognize, by indirect immunohistochemistry, a cytoplasmic antigen expressed specifically, in adult rat brain, by a subpopulation of oligodendrocytes of the brain stem, the medulla and the cerebellum.

The originality of these auto-antibodies resides, on the other hand, in their diagnostic interest. Their presence in the serum or the CSF of patients is of diagnostic value because it allows the paraneoplastic origin of a neurological syndrome to be specified. The discovery of these antibodies, when it precedes that of cancer, directs the search to that and allows its discovery. Such was the case for six patients out of 19 having anti-CV2 antibodies. The clinical disorders were different according to the patients, certain of them having a picture of limbic encephalitis, others encephalomyeloneuritis and others Lambert-Eaton syndrome. Nevertheless, in more than 60% of the cases, the cerebellar syndrome was predominant. The most frequently associated tumour was small-cell lung cancer (60% of the cases).

Experiments on the brains of newborn rats showed that these anti-CV2 antibodies reacted with a protein of 66 kDa (Honnorat et al., 1996).

In the adult brain, this antigen is situated in a subpopulation of oligodendrocytes or in cells which retain differentiation capacities in the adult brain (olfactory bulb, dentate gyrus). The recognized antigen could play a role in neuronal survival, via Neuron/Oligodendrocyte interactions, as the loss of neurons observed in the post-mortem brain of patients suffering from PNS suggests.

Its very limited expression in adulthood contrasts with a very strong and transitory expression in the central and peripheral nervous system in development, suggesting the probable role of this antigen in the development of the nervous system.

The Applicant has characterized the target antigen of anti-CV2 antibodies, which corresponds to a protein designated below by "POP-66" for "paraneoplastic oligodendrocyte protein 66 kDa".

Surprisingly, it has been discovered that the POP-66 protein belongs to the so-called ULIP family of proteins (for Unc-33-like phosphoprotein), involved in the control of neuronal development and axonal transport (T. Byk et al., 1996), and also studied in the form of CRMP proteins (Goshima et al., 1995, Wang et al., 1996), TOAD-64 (Minturn et al., 1995) and DRPs (Hamajima et al., 1996). More precisely, POP-66 has been identified as in fact being the human form of ULIP-4.

All of the data described below emphasize the complexity of this family of proteins, the existence of a very wide expression spectrum of members of this family in the brain in the course of ontogenesis, but a very limited spectrum in adults, as well as the specificity of the anti-CV2 antibodies for a member of this ULIP protein family, which is in fact POP-66.

SUMMARY OF THE INVENTION

Thus, the Applicant has shown that the protein recognized by the anti-CV2 antibodies of patients suffering from PNS is POP-66/ULIP-4 and has established the involvement of the ULIP proteins in paraneoplastic neurological syndromes and associated cancers. In addition to their role in cancers associated with PNS, the Applicant has likewise discovered that the proteins of the ULIP family could play a role in any other form of cancer not associated with PNS. More particularly, the ULIP proteins could especially be involved in cancers of tissues having a common embryonic origin with the central nervous system.

The present invention therefore relates to a purified ULIP polypeptide, derivative or polypeptide fragment of the said purified polypeptide, comprising an amino acid sequence selected from SEQ ID No. 2, No. 4, No. 6 and No. 8.

Preferentially, the present invention relates to a purified polypeptide, derivative, or biologically active polypeptide fragment of the said purified polypeptide, comprising the amino acid sequence SEQ ID No. 8, the said polypeptide being designated by "POP-66/ULIP-4".

A fragment of the polypeptide of sequence SEQ ID No. 8 of interest is, in particular, the antigenic fragment PARASCPGKIS (amino acids No. 517 to No. 527).

In the description of the invention, the following definitions are used:
   derivative: any variant polypeptide of the polypeptide of sequence SEQ No, 2, No. 4, No. 6 or No, 8 or any other molecule resulting from a modification of genetic and/or chemical nature of the sequence SEQ ID No. 2, No. 4, No. 6 or No. 8, that is to say obtained by mutation, deletion, addition, substitution and/or chemical modification of a single or of a limited number of amino acids, as well as any isoform sequence, that is to say a sequence identical to the sequence SEQ ID No. 2, No. 4, No. 6 or No. 8, to one of its fragments or modified sequences, containing one or more amino acids in the D enantiomer form, the said modified or isoform variant sequences having conserved at least one of the properties making them biologically active.
   biologically active: having properties of induction and/or control of neuronal development and/or antigenic properties.

The invention likewise relates to an isolated nucleic acid sequence selected from SEQ ID No. 1, No. 3, No. 5 and No. 7 or a sequence derived from the sequences SEQ ID No. 1; No. 3; No 5 and No. 7 on account of the degeneracy of the genetic code, or on account of mutation, of deletion or of insertion of at least one nucleotide, the said derived sequences having a biological activity virtually identical to that of the peptide encoded by the sequences SEQ ID No. 1, No. 3, No. 5 and No. 7.

The various nucleotide sequences of the invention can be of artificial or non-artificial origin, They can be DNA or RNA sequences, obtained by screening of banks of sequences by means of probes elaborated on the basis of sequences selected from SEQ ID No. 2, No. 4, No. 6 and No. 8. Such banks can be prepared by conventional techniques of molecular biology known to the person skilled in the art.

The nucleotide sequences according to the invention can likewise be prepared by chemical synthesis, or alternatively by mixed methods including the chemical or enzymatic modification of sequences obtained by screening of banks.

These nucleotide sequences allow the production of nucleotide probes capable of hybridizing strongly and specifically with a nucleic acid sequence of a genomic DNA or of a messenger RNA coding for a peptide according to the invention or a biologically active fragment of this. The appropriate hybridization conditions correspond to the conditions of temperature and of ionic strength usually used by the person skilled in the art (Sambrook et al., 1989), preferably to temperature conditions of between ($T_m$ minus 5° C.) and $T_m$ minus 30° C.) and more preferably to temperature conditions of between ($T_m$ minus 5° C.) and ($T_m$ minus 10° C.) (great stringency), $T_m$ being the theoretical melting point, defined as being the temperature at which 50% of the paired strands separate. Such probes are likewise part of the invention. They can be used as a diagnostic tool in vitro for the detection, by hybridization experiments, of specific transcripts of polypeptides of the invention in biological samples or for the demonstration of aberrant syntheses or genetic anomalies resulting from polymorphism, mutations or bad splicing.

The probes of the invention contain at least 10 nucleotides, and at most contain the whole of a nucleotide sequence selected from SEQ ID No. 1, No. 3, No. 5 and No. 7 or of their complementary strand.

The in vitro diagnostic methods in which these nucleotide probes are employed for the detection of aberrant syntheses or genetic anomalies, such as the loss of heterozygosity and genetic rearrangement, at the level of nucleic sequences coding for a ULIP polypeptide according to the invention or a biologically active fragment are included in the present invention. Such a method type comprises:
   the contacting of a nucleotide probe of the invention with a biological sample under conditions allowing the formation of a hybridization complex between the said probe and the abovementioned nucleotide sequence, optimally after a previous amplification step of the abovementioned nucleotide sequence;
   the detection of the hybridization complex optimally formed;
   optimally the sequencing of the nucleotide sequence forming the hybridization complex with the probe of the invention.

The cDNA probes of the invention can additionally be advantageously used for the detection of chromosomal anomalies.

The nucleotide sequences according to the invention are likewise useful for the production and use of sense and/or antisense oligonucleotide primers for sequencing reactions or specific amplification reactions according to the so-called PCR technique (polymerization chain reaction) or any other variant of this.

The nucleotide sequences according to the invention additionally have uses in the therapeutic field, for the production of antisense sequences capable of hybridizing specifically with a nucleic acid sequence, including a messenger RNA, which can be used in gene therapy. The invention thus relates to antisense sequences capable of inhibiting, at least partially, the production of a polypeptide according to the invention, such as defined above.

They are more particularly useful in the treatment of disorders of the central and peripheral nervous system and of vision, especially in the treatment of paraneoplastic neurological syndromes, as well as in anti-cancer treatment, especially of tumours associated with paraneoplastic neurological syndromes.

The nucleotide sequences according to the invention can additionally be used for the production of recombinant ULIP proteins according to the invention.

These proteins can be produced from nucleotide sequences defined above, according to techniques of production of recombinant products known to the person skilled in the art. In this case, the nucleotide sequence used is placed under the control of signals allowing its expression in a cell host.

An efficacious system of production of a recombinant protein necessitates having a vector, for example of plasmid or viral origin, and a compatible host cell.

The cell host can be selected from prokaryotic systems, such as bacteria, or eukaryotic systems, such as, for example, yeasts, insect cells, CHO (Chinese hamster ovary) cells or any other system advantageously available. A preferred cell host for the expression of proteins of the invention is formed by the bacterium E. coli.

The vector must contain a promoter, translation initiation and termination signals, as well as the appropriate regions of transcription regulation. It must be able to be maintained stably in the cell and can possibly possess special signals specifying the secretion of the translated protein.

These different control signals are selected as a function of the cell host used. To this end, the nucleotide sequences according to the invention can be inserted in autonomous replication vectors within the selected host, or integrative vectors of the selected host. Such vectors will be prepared according to methods currently used by the person skilled in the art, and the resulting clones can be introduced into an appropriate host by standard methods, such as, for example, electroporation.

The invention is additionally directed at the host cells transfected by these above vectors. These cells can be obtained by the introduction into host cells of a nucleotide sequence inserted into a vector such as defined above, then the culturing of the said cells under conditions allowing the replication and/or expression of the transfected nucleotide sequence.

These cells can be used in a method of production of a recombinant polypeptide according to the invention or any fragment or biologically active derivative of this.

The method of production of a polypeptide of the invention in recombinant form is itself included in the present invention, and is characterized in that the transfected cells are cultured under conditions allowing the expression of a recombinant polypeptide according to the invention or of any fragment or biologically active derivative of this, and in that the said recombinant polypeptide is recovered.

The purification processes used are known to the person skilled in the art. The recombinant polypeptide can be purified from lysates and cell extracts, from the supernatant of the culture medium, by methods used separately or in combination, such as fractionation, chromatographic methods, immunoaffinity techniques with the aid of specific mono- or polyclonal antibodies, etc:

One variant consists in producing a recombinant polypeptide fused to a "carrier" protein (chimeric protein). The advantage of this system is that it allows a stabilization and a decrease in the proteolysis of the recombinant product, an increase in the solubility in the course of the in vitro renaturation and/or a simplification of the purification when the fusion component has an affinity for a specific ligand.

The exploitation of ULIP proteins, and in particular POP-66/ULIP-4, as well as antibodies directed against these proteins, is promising in various fields.

Thus, the detection of the anti-CV2 auto-antibody by immunofluorescence on fixed animal brain is currently used as a diagnostic test.

The production of POP-66/ULIP-4 recombinant protein according to the invention allows the production of a rapid and reliable test (of Elisa or Western Blot type) for detecting anti-CV2 antibodies.

Such tests already exist for anti-Hu, anti-Yo and anti-Ri antibodies. The test for detecting anti-CV2 in the serum of patients could be prescribed in the case of suspicion of paraneoplastic neurological syndrome and consequently could include anti-CV2 antibodies at the same titre as the other antibodies identified in the PNS such as mentioned above.

The invention is therefore likewise directed at a method for the diagnosis of paraneoplastic neurological syndromes and/or for the early diagnosis of the formation of tumours of cancerous origin, characterized in that auto-antibodies directed against a POP-66/ULIP-4 protein are demonstrated in a blood sample taken from an individual by the contacting of a blood sample taken from an individual with a purified polypeptide (POP-66), derivative or biologically active polypeptide fragment of POP-66/ULIP-4 optionally attached to a support under conditions allowing the formation of specific immunological complexes between the said polypeptide and the auto-antibodies optionally present in the serum sample, and the detection of the specific immunological complexes optionally formed.

The invention likewise relates to a kit for the diagnosis of paraneoplastic neurological syndromes and for the early diagnosis of the formation of tumours from a biological sample, comprising:

at least one purified POP-66/ULIP-4 polypeptide, derivative or biologically active polypeptide fragment of POP-66/ULIP-4, optionally attached to a support, means of visualization of the formation of specific antigen/antibody complexes between an anti-POP-66 auto-antibody and the said purified POP-66 polypeptide, derivative or polypeptide fragment and/or means of quantification of these complexes.

The invention likewise relates to mono- or polyclonal antibodies or their fragments, chimeric or immunoconjugated antibodies obtained from a purified ULIP polypeptide comprising an amino acid sequence selected from SEQ ID No. 2, No. 4, No. 6 and No. 8, derivative or biologically active polypeptide fragment of ULIP and their use for the purification or the detection of a ULIP protein in a biological sample.

Polyclonal antibodies can be obtained from the serum of an animal immunized against the protein, produced, for example, by genetic recombination according to the method described above, according to the usual working methods.

The monoclonal antibodies can be obtained according to the conventional method of hybridoma culture described by Köhler and Milstein.

The antibodies can be chimeric antibodies, humanized antibodies, Fab and F(ab')$_2$ fragments. They can likewise be present in the form of immunoconjugates or labelled antibodies.

The invention likewise relates to the use of antibodies directed against a protein of the ULIP family for the demonstration of a ULIP protein in neoplasms, and paraneoplastic neurological syndromes for diagnostic purposes.

Preferentially, the invention relates to the use of monoclonal antibodies obtained from polyclonal anti-CV2 serum of patients by immortalization of lymphocytes, according to the usual techniques known to the person skilled in the art.

Thus, the antibodies directed against a protein of the ULIP family are useful for detecting abnormal expression of ULIP protein in patients having neurological syndromes, in whom cancer has not been diagnosed by the conventional methods. This abnormal expression of ULIP protein will be able to be correlated with the existence of a cancer which had not been spotted. Thus, the antibodies directed against a ULIP protein, especially against POP-66/ULIP-4, are useful for the early diagnosis of cancer.

The invention likewise relates to a method of determination of an allelic variability, a mutation, a deletion, an insertion, a loss of heterozygosity or a genetic anomaly of the POP-66/ULIP-4 gene, situated on chromosome 10 in the 26q region and which can be involved in pathologies, characterized in that it employs at least one nucleotide sequence SEQ ID No, 7. Amongst the methods of determination of an allelic variability, a mutation, a deletion, an insertion, a loss of heterozygosity or a genetic anomaly of the POP-66/ULIP-4 gene, a method comprising at least one PCR amplification step of the nucleic sequence of POP-66/ULIP-4 capable of having a polymorphism, a mutation, a deletion or an insertion with the aid of pairs of primers of nucleotide sequences, a step in the course of which amplified products are treated with the aid of appropriate restriction enzymes and a step in the course of which at least one of the products of the enzymatic reaction is detected or determined is preferred.

Advantageously, it is possible to search for the mutations associated with the said chromosome 10 in relation to cancer, especially peripheral cancerous tumours and primitive cerebral tumours of glial origin, for example.

The invention likewise relates to a pharmaceutical composition comprising at least one purified protein of the ULIP family, polypeptide fragment or biologically active derivative of this, a nucleotide sequence or nucleotide sequence fragment coding for the said protein, an antisense sequence capable of hybridizing specifically with a nucleotide sequence coding for the said protein, or an antibody directed against the said protein, combined with a pharmaceutically acceptable vehicle.

The invention preferentially comprises pharmaceutical compositions comprising as active principle a purified POP-66 polypeptide, derivative or polypeptide fragment of POP-66, preferentially in soluble form, combined with a pharmaceutically acceptable vehicle.

Such compositions offer a new approach to treating disorders of the central and peripheral nervous system and of vision, and especially paraneoplastic neurological syndromes. In addition, they are useful for treating neurological disorders connected with a neuronal loss and/or an under-expression of ULIP proteins in the nervous system.

Thus, POP-66/ULIP-4 is also of interest in neurodegenerative pathologies such as multisystemic atrophies which are conditions similar to those of PNS and for which an anomaly of an oligodendrocytic subpopulation has been detected (Papp et al., 1992).

The compositions according to the invention are additionally useful in anticancer therapy.

The antibodies directed against one or more ULIP proteins can be combined with antineoplastic agents, thus allowing the targeting of medicaments towards the tumour cells.

They can additionally be combined with a hydrophilic chemical group chosen in such a way so as to cross or not to cross the blood-brain barrier, according to the type of tumour.

The ULIP proteins and in particular POP-66 as well as the nucleotide sequences coding for the said proteins and the antisense sequences or oligonucleotides can be useful in the therapy of any type of cancer in which a gene coding for a ULIP protein is involved. Amongst examples of cancers, it is possible to mention peripheral tumours, such as small-cell lung cancer, thymoma, cancer of the breast and of the ovary, as well as cerebral tumours, preferably primitive cerebral tumours of glial origin. The expression of POP-66 in the non-proliferative cells of normal brain, its absence in normal tissues such as lung or thymus, For example, its differential reexpression during tumorigenesis of these tissues and the modulation of its expression in a tumour line in the course of differentiation suggest in this respect that POP-66 could be a tumour suppressor gene.

Preferentially, the pharmaceutical compositions according to the invention can be administered by the systemic route, preferably by the intravenous route, by the intramuscular route, intradermally or by the oral route.

Their modes of administration, dosages and optimal pharmaceutical forms can be determined according to the criteria generally taken into account in the establishment of a therapeutic treatment adapted to a patient, such as, for example, the age or the body weight of the patient, the seriousness of his/her general condition, the tolerance to the treatment and the secondary effects noted, etc.

The invention likewise comprises the use of a purified protein of the ULIP family, polypeptide fragment or biologically active derivative of this, a nucleotide sequence or nucleotide sequence fragment coding for the said protein, an antisense sequence capable of hybridizing specifically with a nucleotide sequence coding for the said protein, or an antibody directed against the said protein, combined with a pharmaceutically acceptable vehicle, for the production of a medicament intended for treating neurodegenerative illnesses and neoplasms.

The invention finally relates to a method of treatment of neurodegenerative illnesses and neoplasms, comprising the administration to a subject requiring such a treatment of a therapeutically efficacious quantity of a purified protein of the ULIP family, polypeptide fragment or biologically active derivative of this, a nucleotide sequence or nucleotide sequence fragment coding for the said protein, an antisense sequence capable of hybridizing specifically with a nucleotide sequence coding for the said protein, or an antibody directed against the said protein, combined with a pharmaceutically acceptable vehicle.

The examples and the figures whose legends are presented below are given by way of illustration.

A: silver staining of all of the proteins.

B: immunoblot with the anti-CV2 serum of patients.

The arrows indicate the spots corresponding to POP-66, revealed with anti-CV2 antibodies.

Figure 2A:
Figure 2B:
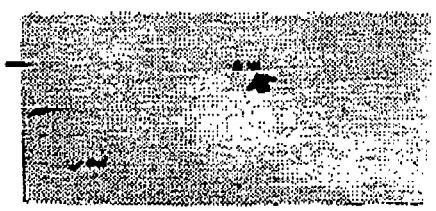

FIG. 2 represents a two-dimensional electrophoresis profile obtained from protein extracts of brains of newborn rats.

Immunoblot with A—antipeptide antibody 3 and B—anti-CV2 antibody.

Figure 3:
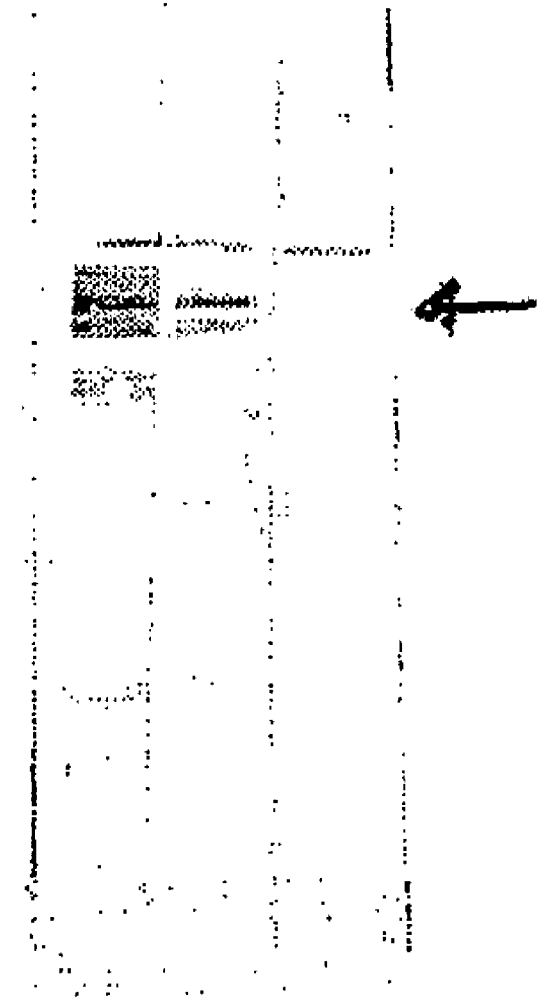

FIG. 3 represents a one-dimensional electrophoresis obtained from protein extracts of brains of newborn rats.

Immunoblot with a: preimmune serum for peptide 3

Immunoblot with b: anti-peptide serum 3

Immunoblot with c; anti-peptide serum 4

Immunoblot with d: preimmune serum for peptide 4.

Figures 4A, 4B, 4C:
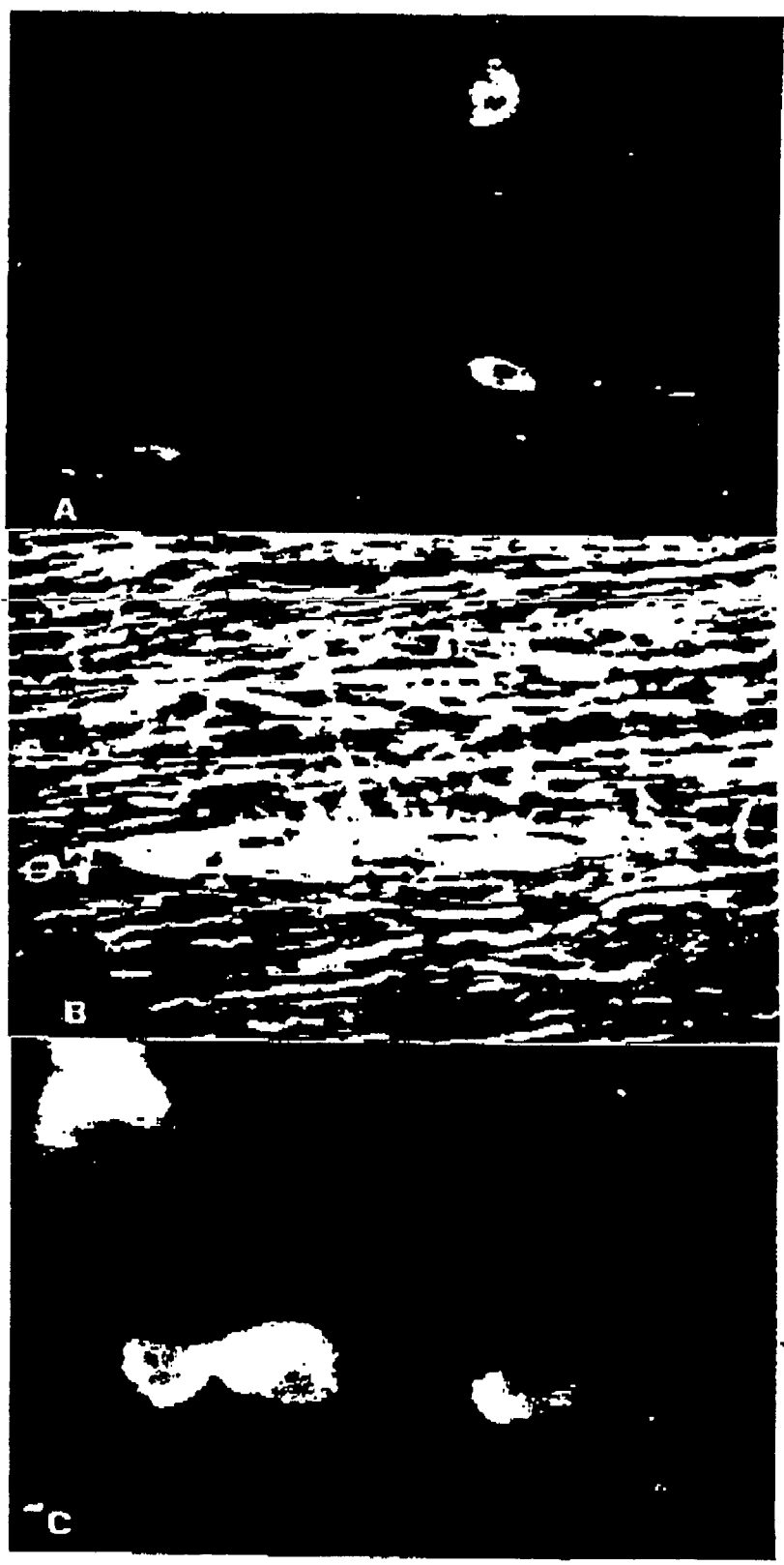
Figure 5A:
Figure 5B:
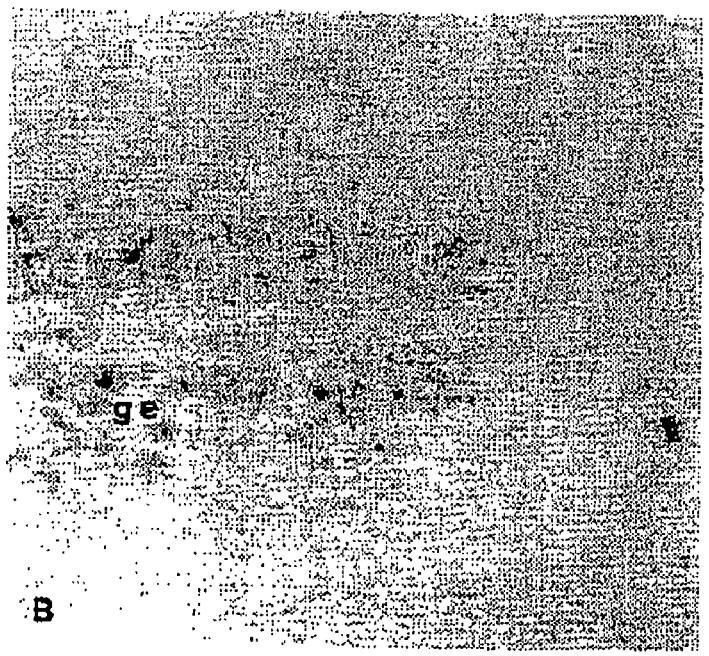
Figure 5C:
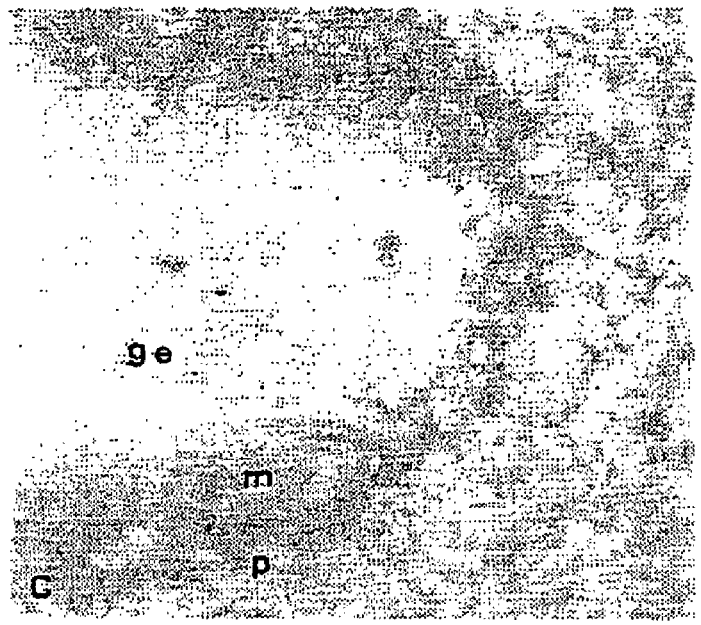
Figure 5D:
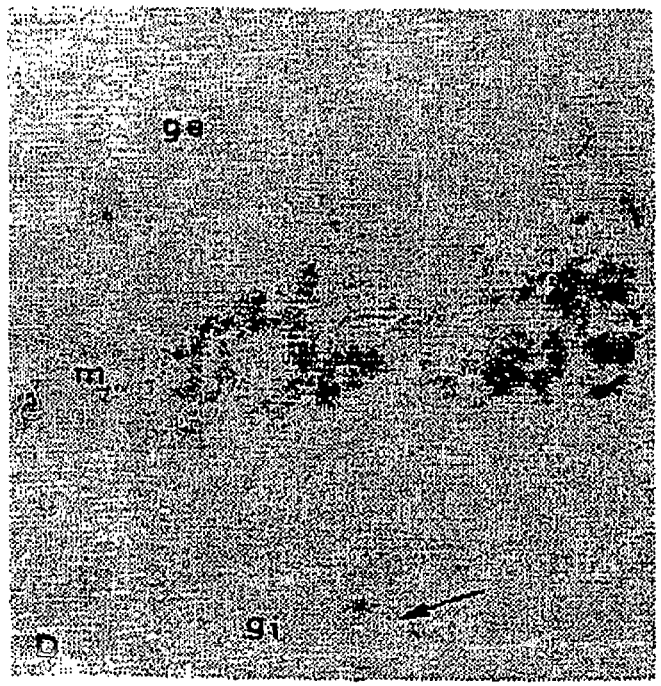

FIG. 4 represents an immunohistochemical labelling of sections of brains of adult rats with A: anti-CV2 serum of a patient suffering from PNS B: rabbit serum with anti-peptide 3 antibodies C; rabbit serum with anti-peptide 4 antibodies.

FIG. 5 represents a histological labelling of sections of young rat cerebellum 8 days post-natally.

A: Staining with toluidine blue; ge=external granular layer; m=molecular layer (×400).

B: Immunolabelling after incorporation of BrdU (bromodeoxyuridine). The cells which have incorporated BrdU are virtually all situated in the most external zone of the external granular layer (ge). Some positive cells are situated in the internal granular layer (×400).

C: Indirect immunoperoxidase with a patient serum containing an anti-CV2 antibody (×400). The immunoreactivity is concentrated in the internal part of the external granular layer (future molecular layer (m)). Some cells are immunoreactive in the internal granular layer. The Purkinje cells (p) are negative as well as the cells of the external part of the external granular layer (ge).

D; Indirect immunoperoxidase with a patient serum containing an anti-CV2 antibody (×1000). Above all, the immunolabelling is concentrated in the internal part of the external granular layer (future molecular layer (m)). A reactive cell is noted in the internal granular layer (gi) (arrow).

Figure 6B:
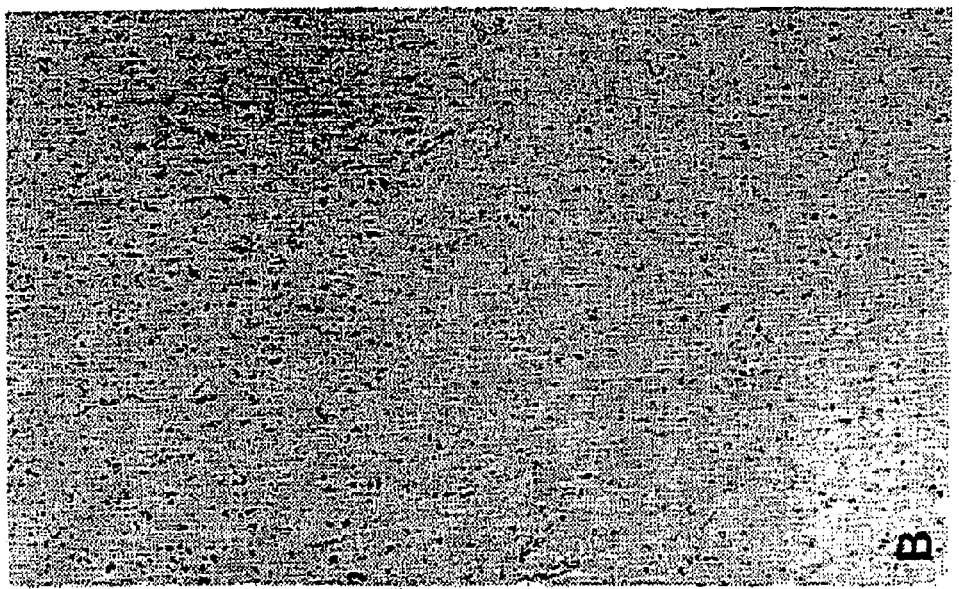
Figure 6A:
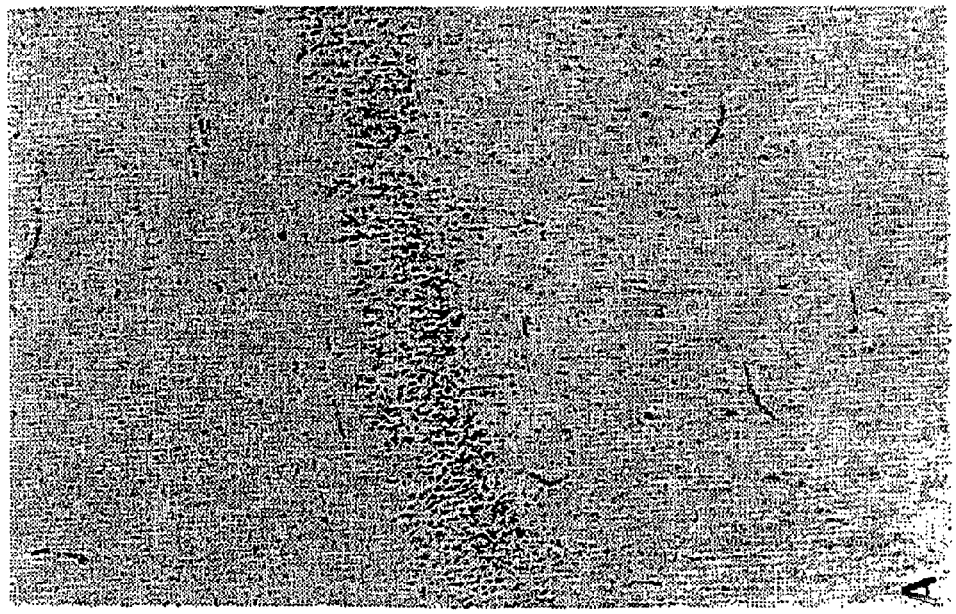

FIG. 6 represents immunohistochemical labelling of sections of post-mortem hippocampus (HPS staining).

A: brain of control patient,

B: brain of patient having limbic encephalitis, and circulating anti-CV2 antibody. It is possible to note the disappearance of the granular cells.

Figures 7A, 7B:
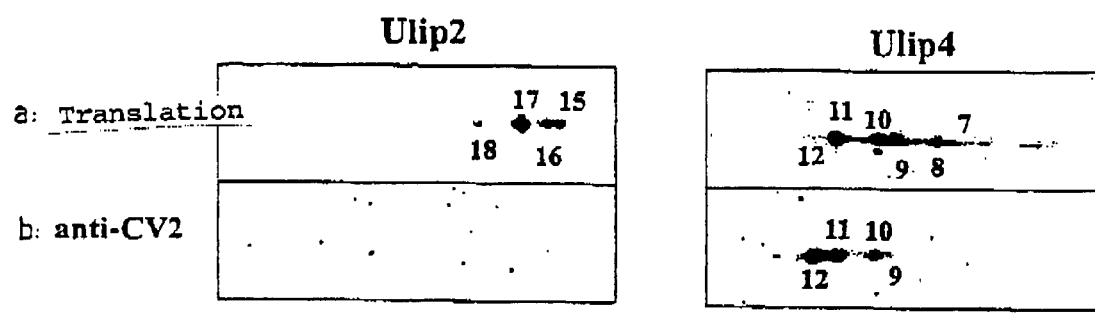

FIG. 7 represents a two-dimensional electrophoresis profile with the control ULIP-2 protein (A) and the ULIP-4 protein (B).

Figure 7C:
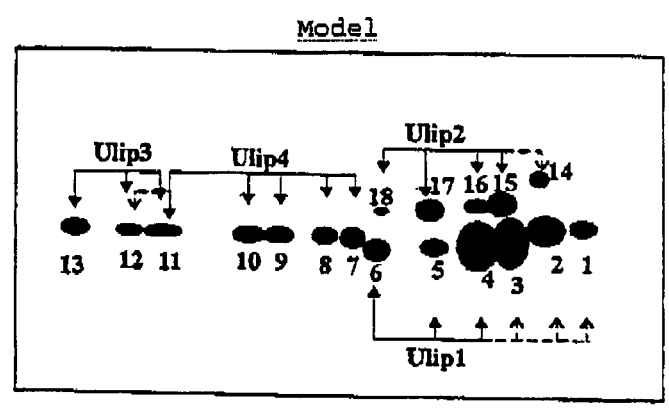

FIG. 7C represents the migration profile model of the proteins ULIP-1, 2, 3 and 4 as a reference.

The proteins are revealed:

a) by autoradiography to locate the proteins translated in vitro (translation);

b) by immunoblotting with the anti-CV2 serum.

Figure 8A:
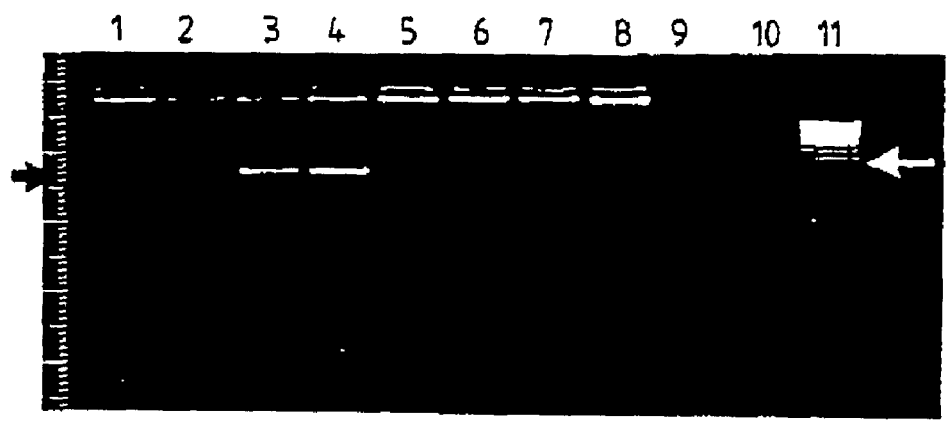
Figure 8B:
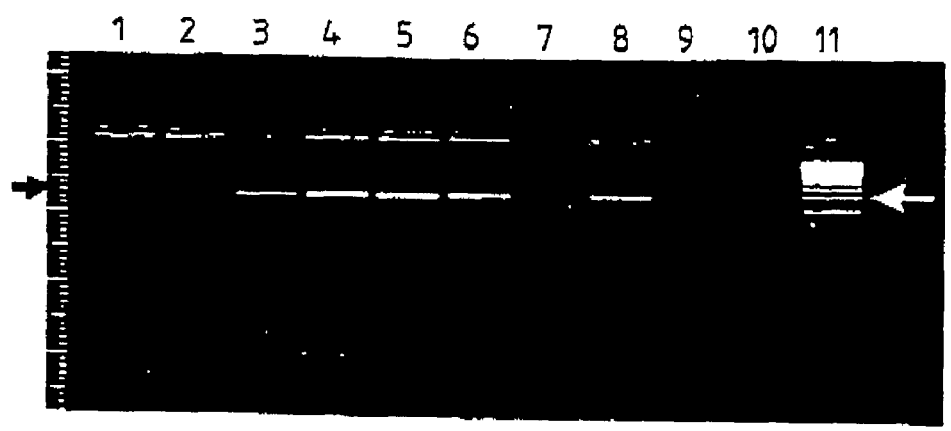

FIG. 8 represents a migration profile of the mRNA of C-22/ULIP-3 (8A) and TOAD-64/ULIP-2 (8B) amplified by RT-PCR expressed in different cell types:

| | |
|---|---|
| lanes 1–3: | small-cell lung tumour |
| lane 2: | small-cell lung tumour with anti-CV2 serum |
| lane 4: | control cDNA. |
| lane 5: | medulloblastoma treated by HTLV1 infection |
| lanes 6–7: | medulloblastoma |
| lane 8: | C6 line of glial cells in mice |
| lane 9: | control |
| lane 10: | nothing |
| lane 11: | kb scale. |

The black arrows correspond to POP-66; the white arrows correspond to the molecular weight standard.

FIGS. 9A–9D represent the nucleotide sequence of ULIP-2 in mice (SEQ ID No. 1), as well as the inferred amino acid sequence (SEQ ID No. 2).

FIGS. 10A–10D represent the nucleotide sequence of ULIP-3 in mice (SEQ ID No. 3), as well as the inferred amino acid sequence (SEQ ID No. 4).

FIGS. 11A–11D represent the nucleotide sequence of ULIP-4 in mice (SEQ ID No. 5), as well as the inferred amino acid sequence (SEQ ID No. 6).

Figure 12C:
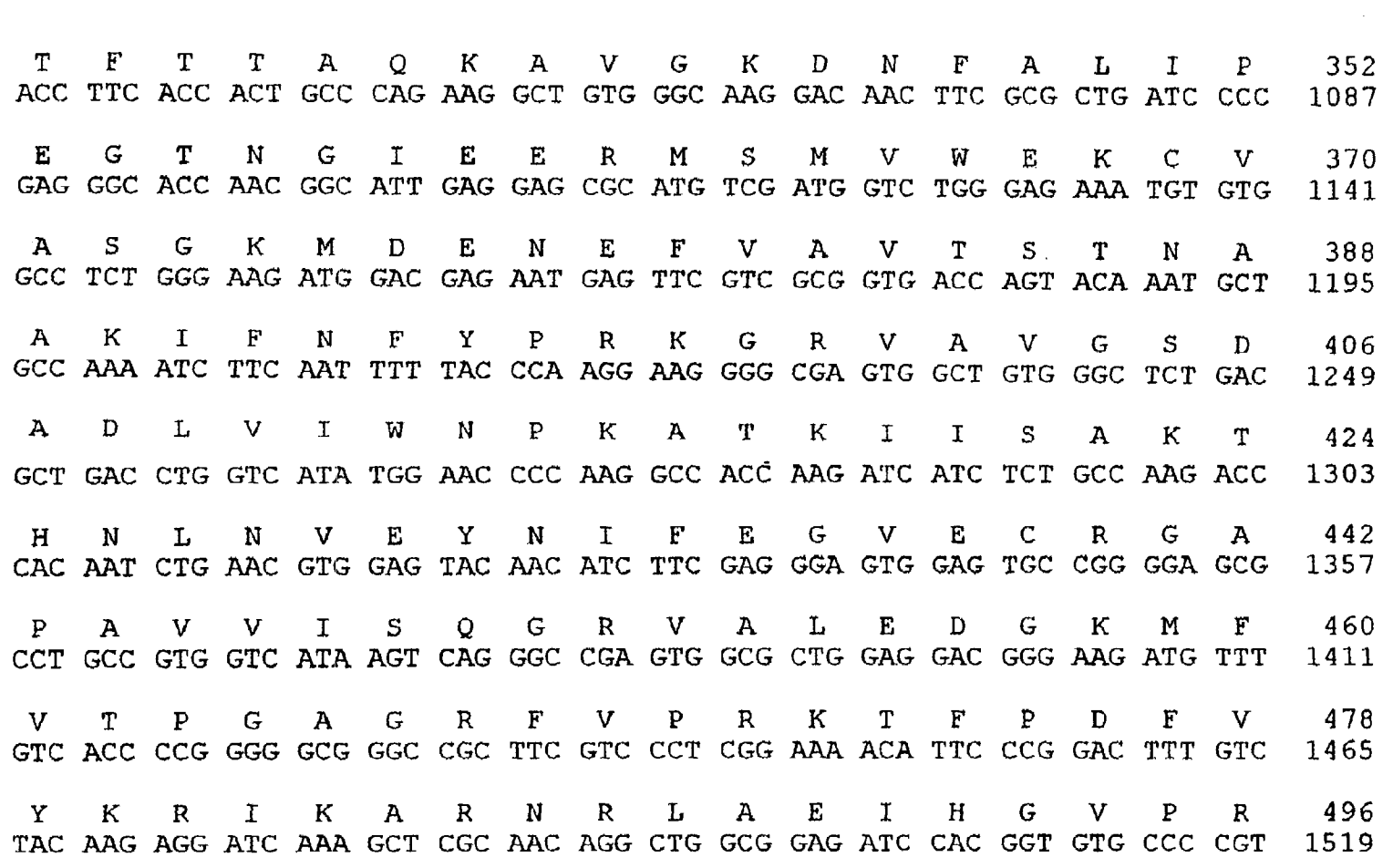

FIGS. 12A–12D represent the nucleotide sequence of ULIP-4 in man (SEQ ID No. 7), as well as SEQ ID No. 9 and SEQ ID No. 10 which provide for the inferred amino acid sequence for amino acid residues 1–55 and 57–553 of SEQ ID No. 8.

An erroneous stop codon in the human ULIP-4 sequence (asterisk) arises from a fault of the reverse transcriptase in the production of the bank. By comparing with ULIP-4 of rats and of mice, it is almost certain that the TAG sequence coding for a stop is in fact an AAG codon, coding for a lysine as in rats and mice. In addition, the region around this amino acid is entirely conserved in the three species.

The amino acid sequence has been completed in SEQ ID No. 8 by 19 C-terminal amino acids (No. 554 to No. 572). This C-terminal region which is missing in FIG. 12 is very well conserved between rat and mice ULIP-4 as well as between the different ULIPs. SEQ ID No. 8 is further divided into SEQ ID Nos. 9 and 10 which correspond to amino acids 1 to 55 and 57 to 553, respectively. SEQ ID No. 8 is split into two parts

DETAILED DESCRIPTION OF PREFERRED EMBODIMENTS

The present invention will be described with reference to the following examples

EXAMPLE 1

Purification of POP-66 and Sequencing

The purification of POP-66 is carried out according to the material and the methods described in the article of Honnorat et al., 1996, incorporated by reference, starting from serum of patients suffering from PNS.

To identify the protein POP-66, a purification strategy was chosen which allows a partial sequencing to be obtained. The screening of an expression bank of brain cDNA or the immunoaffinity purification of the protein were excluded because of the limited quantities of sera linked to the death of the patients. It was possible to develop a method of biochemical purification starting from brains of newborn rats on account of the anti-CV2 human sera, which allowed each purification step to be monitored.

The tissues, preserved at −70° C. before use, were treated with a solution containing 0.2 M DTT (dithiothreitol) (Sigma) 2% Ampholine 3–10 (Pharmacia), 2% Triton X-100 (Merck) and placed at 2–4° C. Immediately before use, solid urea (Pharmacia) was added to obtain an 8M solution.

The POP-66 protein is soluble, at least in part, and precipitates entirely at a concentration of 40% ammonium sulphate.

Centrifugation at 100,000 (times) g and ammonium sulphate precipitation (eliminating the proteins precipitating below 20% and above 40% ammonium sulphate) allows protein extracts enriched in POP-66 to be obtained. The proteins of this extract are then separated, after dialysis, by isofocussing on agarose gel (Peltre et al., 1982).

After transfer to a membrane, the anti-CV2 antibodies recognize several bands of isoelectric points of between 5.85 and 6.55. All of these bands correspond to the POP-66 protein recognized by the anti-CV2 antibodies. This spectrum suggests the possibility of transcriptional modifications (phosphorylations and/or glycosylations) of the protein.

The zone of proteins of pI between 5.85 and 6.55 from the agarose gel is used for a new electrophoretic migration in denaturating medium on polyacrylamide gel previously equilibrated with an equilibration solution (0.05 mol/l Tris/HCl, pH 6.8, 6M urea, 30% glycerol, 1% weight/volume SDS for 2×10 minutes) to which is added DTT (0.25% weight/volume) and bromophenol blue.

Two methods of detection are used:
- silver staining. Immediately after the end of the migration, the gel is immersed in a fixing solution (40% ethanol, 10% acetic acid) for 30 minutes; it is then placed in an incubation solution (30% ethanol, 7% weight/volume of sodium acetate, 0.1% glutaraldehyde, 0.2% weight/volume of sodium thiosulphate) for 30 minutes or one night. After washing, the gel is placed in a silver solution (0.1% weight/volume of silver nitrate+formaldehyde) and developed (2.5% weight/volume of sodium carbonate+formaldehyde). The reaction is stopped with Na$_2$ EDNA (1.5% weight/volume). The gels are preserved in a glycerol solution.
- transfer to a PVDF membrane (Immobilon-P®, Millipore). The separated proteins are transferred to a PVDF membrane using a 100 mM CAPS buffer (Sigma) of pH 11. The transfers are incubated for one hour in TBS buffer (Tris buffer saline) with 5% of casein (milk) and 18 hours in TBS buffer (+1% of casein) containing antibody (1/500 anti-CV2 serum). After washing with TBS-casein (15 minutes), visualization is carried out by incubating the transfers for 1 and a half hours with biotinylated anti-IgG antibodies (1/1000) and for 1 and a half hours with the streptavidin-peroxidase complex (1/2000). The transfers are then visualized with DAB (0.06% weight/volume diaminobenzidine in 0.05 M Tris) and with H$_2$O$_2$ (0.02 µg/ml).

Figure 1A:
FIG. 1 represents a two-dimensional electrophoresis profile obtained from brain protein extracts of newborn rats enriched in POP-66.
Figure 1B:

A single band corresponding to a protein of 66 kDa is visible. This is specifically labelled with anti-CV2 antibodies (FIG. 1). An N-terminal sequencing of this protein was then carried out, after trypsic digestion.

Seven peptides, having the following sequences, were obtained:

1 - X-Met-Tyr-Asp-Gly-Pro (SEQ ID No. 11)
2 - X-Phe-Asn-Leu-Tyr-Pro-Arg (SEQ ID No. 12)
3 - X-Val-Leu-Glu-Asp-Gly-Thr-Leu-His-Val-Thr-Glu-Gly (SEQ ID No. 13)

-continued

Seven peptides, having the following sequences, were obtained:

4 - X-Ile-Gly-X-X-Ala-Gln-Val-(His ?)-Ala-Glu-Asn-Gly-X-Ile-Ile-Ala-Glu-Glu-Gln (SEQ ID No. 14)
5 - X-X-Glu-Asn-Gln-Phe-Val-Ala-Val-Thr (SEQ ID No. 15)
6 - X-Val-Asn-Asp-(Asp ?)-Gln-Ser-Phe-Tyr-Ala-Asp-Ile-Tyr-Met-Glu-(Asp ?)-(Gly ?)-Leu-Ile (SEQ ID No. 16)
7 - X-X-X-Phe-Val-Thr-X-Pro-X-Leu-X-Pro (SEQ ID No. 17)

X: corresponds to a non-determined amino acid,
( ?): corresponds to a probable but uncertain amino acid.

According to the analysis of databanks available in 1994, no known protein corresponded to these sequences.

EXAMPLE 2

Cloning of the cDNA of POP-66 or of Related Proteins

The cloning of the cDNA of the POP-66 protein or of related proteins was carried out by using degenerate oligonucleotide probes obtained from fragments of two peptides:

Ile-Ile-Ala-Glu-Glu-Gln (SEQ ID No. 18)

Tyr-Ala-Asp-Ile-Tyr-Met-Glu-(Asp ?) (SEQ ID No. 19)

Four sets of degenerate oligonucleotide primers (sense/antisense) are therefore determined (AT(C/T)ATTGC(T/A)GA(A/G)CA (SEQ ID No. 20);

TG(C/T)TC(T/C)AC(T/A)-GCAT(A/G)AT (SEQ ID No. 21);

TATGC(A/T)GA(C/T)AT(C/T)ATGGA (SEQ ID No. 22);

TCCAT(G/A)TA(G/A)CT-(T/A)GCATA (SEQ ID No. 23), and used for a PCR amplification.

The matrix is prepared in the form of double-stranded cDNA (PROMEGA kit) from poly(A+)RNA extracted from the brain of rats 10 days old (Zivic-Miller, USA) using the FAST TRACK mRNA isolation kit (Invitrogen).

The conditions of amplification by PCR are as follows: 35 cycles at 94° C., 1 minute for denaturation, 55° C., 1 minute for hybridization and 72° C., two minutes, for extension.

The PCR products are analysed by 1% agarose gel electrophoresis, electroeluted, cloned in a TA cloning vector (Invitrogen) and sequenced using the primer sites of the T7 and SP6 promoters.

The sequence of amino acids inferred from the MFB-17 clone agrees with the sequences of the two original peptides of POP-66 determined by the analysis of the amino acid sequence.

A comparative analysis of the nucleic acid sequences using the GENBANK and EMBL databases reveals that MFB-17 is a partial cDNA with a nucleotide sequence identical to that of a segment of TOAD-64, a rat neuronal protein (Minturn et al., 1995).

The amino acid sequence inferred in the cDNA of TOAD-64 agrees with the sequences of the seven peptides determined by partial sequence analysis of the protein recognized by the anti-CV2 antibodies after purification by electrophoresis.

The molecular weight, the isoelectric point, the immunohistochemical profile and the regulation of TOAD-64 are similar to those of the POP-66 antigen.

Since the MFB-17 clone did not have the complete coding region, it was necessary to produce an intact recombinant protein to continue the research concerning the CV2 protein.

To obtain a complete TOAD-64 protein, the ds-cDNA matrix of rat brains was amplified with two sets of primers situated at the 5' and 3' extremities of the coding regions (sense: GGCATATGTCTTATCAGGGGAAG (SEQ ID No. 24);

antisense: GCGAATTCTTAGCCCAGGCTGATG (SEQ ID No. 25)).

This approach allowed two different clones to be produced, one corresponding to the TOAD-64 sequence and the other to a clone designated by C-22.

EXAMPLE 3

Comparison of the Amino Acid Sequence Inferred from C-22 with the ULIP Proteins

The amino acid sequence inferred from the open reading frame indicates that this C-22 clone belongs to the superfamily of ULIP genes represented by several genes of EST sequences.

The amino acid sequence inferred from C-22 has a homology of 30% with the amino acid sequence of the unc-33 protein of *Caenorhabditis elegans*.

Recently, four homologous genes in the unc-33 protein have been described in mammals and the chicken.

An analysis of the sequences by the Genbank databases and protein banks has allowed a classification of the unc-33-like (ULIP) proteins into four different subgroups to be proposed (Byk et al. 1996).

However, as the real functions of these proteins are not clearly known, the proposed classification is simply based on the percentage of identity of amino acids. ULIP-1 is represented by a mouse "unc-33-like" phosphoprotein which has a homology of 76% with TOAD-64, Crmp-62 and Munc, a mouse sequence recently available from Genbank.

ULIP-2 is composed of TOAD-64, Crmp-62 and Munc which between them have a 97% amino acid identity.

The partial human EST sequences, that is to say hcrmp-1, which have a 75% identity with ULIP-1 or ULIP-2, have been found. They belong to a third group called ULIP-3. The last group identified called ULIP-4 comprises r-CRMP-3 in the rat and the forms ULIP-4 in the mouse and POP-66/ULIP-4 in man.

The comparison of the amino acid sequence of the three ULIP genes, namely TOAD-64 in the rat, Crmp-62 in the chicken and ULIP-1 in the mouse, with the amino acid sequence inferred from the open reading frame of the present C-22 clone, using the Clustal V alignment software program reveals that C-22 has an identity of 74% with ULIP-1, 77% with Crmp-62 and 76% with TOAD-64.

The nucleotide sequence C-22 has an identity of 97% with the partial sequence EST, hCrmp-1, and thus defines the third member of the ULIP-3 group. The TOAD-64, Crmp-62 and C-22 genes each code for a protein of 572 amino acids in length, whereas the amino acid sequence inferred from ULIP-1 gives a protein of 570 amino acids.

The analysis of the amino acid sequence of C-22 domain suggesting that the product(s) of the C-22 gene could be localized in the cytoplasm of the cells.

Several consensus sites of phosphorylation by the kinase C protein (S/T×R/K) appear along the length of the product of the C-22 gene. These observations suggest that C-22 is a phosphoprotein and that the slight differences in the phosphorylation could dictate the activity or the role of different members of this family of proteins throughout the cell cycle.

TABLE I

Summary of proteins having a homology with the ULIPs.

| Family | | Species | EMBL No. |
|---|---|---|---|
| Nematode Unc-33 | | Nematode | Z14146 |
| Dihydropyrimidinase | Hu DHPase | human | D78011 |
| | Ra DHPase | rat | D63704 |
| ULIP-1 group | Ulip | mouse | X87817 |
| | Hu DRP3 | human | D78014 |
| | r-CRMP-1 | rat | U52102 |
| | Hu-Ulip | human | Y07818 |
| ULIP-2 group | ULIP-2 | mouse | SEQ ID No. 2 |
| | Toad-64 | rat | Z46882 |
| | CRMP-62 | chicken | U17277 |
| | Munc | mouse | X87242 |
| | HCRMP-2 | human | U17279 |
| | Hu DRP-2 | human | D78013 |
| | r-CRMP-4 | rat | U52104 |
| ULIP-3 group | ULIP-3 | mouse | SEQ ID No. 4 |
| | HCRMP-1 | human | U17278 |
| | rCRMP-1 | rat | U52102 |
| | C-22 | rat | U52095 |
| | Hu DRP-1 | human | D78012 |
| ULIP-4 group | ULIP-4 | mouse | SEQ ID No. 6 |
| | POP-66/ULIP-4 | man | SEQ ID No. 8 |
| | r-CRMP-3 | rat | U52103 |

EXAMPLE 4

Regulation of the Expression of the C-22 Gene:

The evaluation of alterations in the expression of the C-22 gene could have considerable significance for the knowledge of the functional aspects of the C-22 protein.

Consequently, the Applicant studied the possible regulation of the expression of the C-22 gene in the course of development. The total RNA is extracted and separated by electrophoresis on 1% agarose gel and transferred to Nytran membrane (Duchemin et al. 1987). The transfers are hybridized with a C-22 coding sequence labelled with $^{32}P$, a 0.5 mm phosphate buffer and 5% SDS at 65° C. for 16 hours.

At the end of the hybridization, the transfers are washed successively three times with 2×SSC, 0.1% SDS at ambient temperature, then 1×SSC, 0.1% SDS at 65° C. for 60 minutes, and exposed to X-rays.

Under the conditions used, a single band at 3.8 kb was detected representing the C-22 mRNA which is also the smallest transcript of the unc-33 family of genes of vertebrates. The size of the transcript remains the same during the pre- and post-natal periods.

The kinetics of the C-22 gene in the brain of rats in the course of development shows that the messenger is detectable in the course of the embryonic period on day E17. The quantity of C-22 transcripts increases up to day 7 postnatally then decreases rapidly from the second week after birth to a virtually undetectable level in the adult.

Around birth, a still unknown regulation signal is probably received, which increases the expression of the C-22 gene, this signal being temporarily linked to neuronal differentiation and to axonal development.

The mRNA of C-22 has not been able to be detected by Northern Blot analysis in several regions of the brain such as the frontal cortex, the midbrain and the thalamus in adults and rats more than two years old.

In addition, it has not been possible to detect the mRNA of C-22 in non-neuronal tissues, such as the heart, the lung, the liver and the kidney in one-week old rats and adult rats.

The data on the expression profile of the mRNA of C-22 suggests a decisive role of the C-22 protein in the development of the brain.

EXAMPLE 5

Immunoblotting of POP-66:
A—Materials and Methods
Transfection of the ULIPs in *E. coli*

The full-length cDNAs of rat ULIP-2 and ULIP-3 and mouse ULIP-1 and ULIP-4 were subcloned directionally in the *E. coli* pET-21a(+) expression vector after introduction of a 5'Nde I site and of a 3' EcoRI site by PCR, and the four constructs were resequenced. The expression of the target gene induced by IPTG was carried out according to the protocol of the manufacturer (Novagen).

Production of Anti-ULIP Antibodies

Rabbit antibodies (anti-Pep3) are directed against the peptide ITGPEGHVLSRPEEVE (amino acids 217–232 of the sequence SEQ ID No. 8), synthesized in a multiple peptide synthesis apparatus using F-moc (432A Peptide Synthesizer SYNERGY, Applied Biosystems). The purity was checked by analysis of the sequence by HPLC and mass spectrometry. 1 mg of the synthetic peptide conjugated to limpet haemocyanin, in complete Freund's adjuvant, was used to immunize rabbits with a booster dose of 0.5 mg of bound peptide in complete Freund's adjuvant after 4 weeks. The anti-Pep3 antibodies recognized the four recombinant ULIP proteins expressed in *E. coli*.

Labelling with the anti-Pep3 antibodies was removed after preincubation with peptide 3. Controls with pre-immune rabbit sera were negative.

Anti-peptide 4 antibodies directed against the peptide LEDGTLHVTEGS (SEQ ID No. 26) were produced according to the same protocol.

B—Results

Antibodies against four of the sequenced peptides were products. Two of the sera turned out to be of particular interest.

One contains antibodies (Ac anti-pep3) which recognize several members of the ULIP family on two-dimensional electrophoresis of protein extracts of newborn rat brain (FIG. 2) and on one-dimensional electrophoresis (FIG. 3). On Western Blotting, another antibody (Ac anti-Pep4) recognizes a single band of 66 kDA capable of corresponding to a single member of the family (FIG. 3), namely ULIP-2.

EXAMPLE 6

Immunohistochemistry

The tissue preparations for immunohistochemistry are obtained from newborn rat brains and from post-mortem human brains, fixed at 4° C. in 4% paraformaldehyde and 0.2% picric acid diluted in phosphate buffer (0.1 M, pH=7.4), then cryoprotected.

Immunocytochemistry can be carried out by the indirect immunofluorescence technique. Sections of 12 µm in thickness are prepared in a cryostat and then mounted on gelatin-covered slides, treated with 0.1% Triton X100 for 2 hours in PBS buffer and 1% bovine serum albumin (BSA) and incubated for 12 h with anti-CV2 serum of patients in PBS/1% BSA at ambient temperature (1/100 dilution of the serum). After several washes with PBS/1% BSA, the sections are incubated for 2 h with a rabbit anti-human antiserum conjugated to fluoroscein, diluted to 1% (Dakopatts) in PSB/1% BSA. After washing in PBS, the slides are examined under the microscope. The control sections are incubated either with anti-human IgG antiserum conjugated to fluoroscein alone, or PBS/1% BSA alone, or the patient serum alone, or finally the control serum (patients not suffering from PNS) and antibodies conjugated to fluoroescein at the same dilution.

To confirm the immunofluorescence, it is possible to use indirect labelling by immunoperoxidase. The frozen tissue sections fixed with paraformaldehyde are incubated with 0.3% $H_2O_2$ (to destroy the intrinsic peroxidase activity) and 10% normal rabbit serum (to avoid the non-specific binding of the rabbit IgG) or 1% BSA. After incubation for 12 h with patient sera diluted to 1/1000 and washing, the sections are incubated for 2 h with biotinylated rabbit anti-human IgG antiserum diluted to 1/1000 in PBS/1% BSA. The bound human IgGs are visualized by incubation with an avidin-biotin-peroxidase complex (vectastain ABC complex, Vector) and developed with 0.05% DAB (Sigma). The control sections are obtained with sera of 15 patients without PNS according to the same protocol.

A—Localization of Proteins of the ULIP Family with the Aid of Antipeptide Antibodies:

Immunohistochemical labelling was carried out on sections of newborn and adult rat brains. The antipeptide-3 antibody recognizes (an) antigen(s) present in several cell types on sections of newborn and adult rat brains (FIG. 4). Like the patient anti-CV2 serum, the anti-peptide-4 antibodies do not allow the demonstration of any antigen on sections of newborn rat brain although they specifically label a subpopulation of oligodendrocytes in adult rat brain (FIG. 4).

B—Expression of POP-66 in the Course of the Normal Development of the Brain:

FIG. 5 shows that the proliferative nerve cells of the progenitor zones of the nervous system demonstrated by the accumulation of bromodeoxyuridine (BrdU) do not express POP-66 although the non-proliferative cells which correspond to the nerve cells in differentiation or in migration express it.

EXAMPLE 7

Role of POP-66 in Neuronal Survival

FIG. 6 allows human brain sections of healthy patients and of patients suffering from PNS to be compared. In the patients suffering from PNS and having circulating anti-CV2 antibodies, a disappearance of the neurons of the dentate gyrus and of pyramidal neurons (central cell band), as well as an intense astrocytic reaction, are observed.

EXAMPLE 8

Characterization of the POP-66 Protein-Identification with ULIP-4:

Materials and Methods a) Partial Purification of ULIP-1

Partially purified ULIP-1 was obtained from newborn mouse brains by three purification steps. These brains were homogenized in 4 volumes of homogenization buffer (25 mM sodium phosphate, pH 7.8, 1 mM EGTA, 10 µg/ml of leupeptin, 25 µg/ml of aprotinin, and 10 µg/ml of pepstatin. The homogenates were centrifuged for 10 minutes at 400×g. The plugs were resuspended in 2 volumes of homogenization buffer, homogenized and centrifuged again. The supernatants from two centrifugations were collected, sonicated and centrifuged for 1 hour at 100,000×g. The supernatant (S2) was loaded onto a column of DEAE-Sepharose CL-6B (1.75 $cm^2$×26 cm) equilibrated with 100 ml of buffer A (25 mM sodium phosphate, pH 7.8, 1 mM EGTA) at a flow of 30 ml per hour. The proteins were eluted in 300 ml of a 0–250 mM linear gradient of sodium chloride in buffer A and 5 ml samples were collected. The fractions containing ULIP were collected and solid ammonium sulphate was added to 20% saturation. This pool was loaded onto a column of phenyl-Sepharose CL-4B (1.75 cm²×22 cm) which had been previously equilibrated with 100 ml of buffer B (10 mM sodium phosphate, pH 7.8, 1 mM EGTA) containing 20% of saturated ammonium sulphate. The proteins were eluted in a linear gradient decreasing from 20 to 0% of saturated ammonium sulphate in buffer B. The fractions containing ULIP were collected and dialysed twice against 20 volumes of buffer A. The proteins were concentrated in a small (10 ml) column of DEAE-Sepharose CL-6B and eluted with 400 mM sodium chloride in buffer A. The eluate was desalted on a Sephadex G-25 (NAP-10) column and concentrated to a final volume of 0.5 ml by evaporation. In the last purification step, the concentrated fraction was chromatographed in three successive steps, on two Superose™ 12 FPLC (Fast Protein Liquid Chromatography) columns mounted in series, in buffer C (50 mM sodium phosphate, pH 7.2, 150 mM sodium chloride) at a rate of 0.3 ml/minute. The fractions (0.6 ml) were collected and the fractions enriched in ULIP were analysed. The presence of ULIP in the successive purification steps was tested by a one-dimensional Western Blot using an anti-stathmin antibody capable of cross-reactivity. The proteins were quantified according to the method of Bradford.

b) Migration on Electrophoresis Gel:

A one-dimensional electrophoresis was carried out on 13% polyacrylamide gels according to the method of Laemmli. The two-dimensional PAGE electrophoreses were carried out as described above. The isoelectro-focussing gels contained 2% of total ampholines, pH 6–8 and 3–10 in a ratio of 4:1. The second dimension had been carried out on 10% acrylamide gels. The proteins had been either subjected to immunoblotting or stained with silver.

c) Western Blot Analysis:

The proteins were transferred from gels to nitrocellulose in buffer containing 48 mM Tris, 39 mM glycine and 5% of methanol. The membrane was saturated with casein (2.5%) in the immunoblotting solution (12 mM Tris-HCl, pH 7.4, 160 mM NaCl, 0.1% Triton X-100) and tested with an antiserum directed against the peptide I of rat stathmin (1/10,000 dilution) or an antiserum directed against the recombinant ULIP protein (dilution 1/20,000) diluted in an immunoblotting solution containing 1% of casein. The bound antibodies were detected either with a protein A labelled with $^{125}$I and autoradiographed or with anti-rabbit antibodies bound to peroxidase using the ECL kit (Amersham).

d) Analysis of the Protein Sequence:

The fractions enriched in ULIP were separated on polyacrylamide gels in two dimensions. The gels are fixed for 30 minutes in 25% ethanol and 10% acetic acid and stained for 3 minutes in 0.1% amido black in 1% acetic acid and 40% methanol. The gels were decolourized in 1% acetic acid and the spots corresponding to the principal form of ULIP were cut out in these three gels, collected and digested with 2 mg/ml of Lys C endoprotease. The peptides eluted from the gel were then separated by HPLC on a DEAE-C18 column with a gradient of 0–55% of acetonitrile in 0.1% trifluoroacetic acid. The peptides were then sequenced according to the Edman automatic degradation.

e) Expression In Vitro in a Mammal

1 µg of the Bluescript plasmid containing the entire cDNA coding for ULIP-1, ULIP-2, ULIP-3 or ULIP-4 was used to carry out the transcription and translation in vitro with the "Reticulocyte lysate" system (Promega) according to the protocol described by the manufacturer. 5 µg of the total transcription/translation mixture of 25 µl were analysed on electrophoresis gel in two dimensions.

Results

Neither the recombinant protein ULIP-1, nor the recombinant proteins TOAD-64 (ULIP-2) and C-22 (ULIP-3) were recognized by the anti-CV2 sera. In addition, the distribution profile of the spots corresponding to POP-66 recognized by the anti-CV2 antibodies on electrophoresis in two dimensions does not correspond to the spots recognized by the anti-ULIP-1 antibodies. However, POP-66 is a member of the ULIP family since the three POP-66 spots are recognized by the anti-pep3 Ac. POP-66 therefore corresponds to a member of the family of more basic pH$_i$.

After translation in vitro of the four proteins (ULIP-1, 2, 3 and 4), it was shown that ULIP-4 has the same 2D electrophoretic profile as POP-66 and is recognized by the anti-CV2 antibodies (FIG. 7).

For this, the ULIP-4 protein and, as control, the ULIP-2 protein were translated in vitro in the presence of $^{35}$S methionine from cDNA clones coding for the entire proteins. The proteins were separated by two-dimensional electrophoresis (in the presence of a brain extract providing the essential references), transferred to nitrocellulose and visualized:

by autoradiography to localize the proteins translated in vitro (translation);

by immunoblotting with the CV2 serum.

FIG. 7 shows that the three spots from the in vitro translation of ULIP-4 correspond to the spots recognized by CV2. These spots are not recognized in the translation of ULIP-2.

The CV2 serum therefore specifically recognizes ULIP-4. This allowed POP-66 to be identified like ULIP-4.

EXAMPLE 9

Chromosomal Localization of the POP-66/ULIP-4 Protein

Having cloned the cDNA of human ULIP-4, it is then possible to determine the chromosomal localization of the POP-66/ULIP-4 gene by genetic mapping by in situ isotopic hybridization (Levy and Mattei et al., 1995).

In situ hybridization is carried out on preparations of chromosomes obtained from human lymphocytes stimulated by phytohaemagglutinin cultured for 72 hours. 5-Bromodeoxyuridine was added during the last 7 hours of culture (60 µg/ml of medium) to ensure a post-hybridization image of chromosome bands of good quality. The clone containing an insert of 1300 base pairs coding for ULIP-4 in the Bluescript vector is labelled with tritium by nick translation with a specific activity of 1×10$^8$ dpm. µg$^{-1}$. The radiolabelled probe was hybridized in the metaphase stage at a final concentration of 200 ng per ml of hybridization solution. After covering with a Kodak NTB$_2$ emulsion, the slides were exposed for 20 days at +4° C. and then developed. To avoid the shifting of the silver grains during the process, the chromosome blots were previously labelled with a Giemsa buffer solution and the metaphases were photographed. The visualization of the bands was carried out by the "Giemsa fluorochrome photolysis" (FPG) method and the metaphases were rephotographed before analysis. Of the 100 cells in metaphase examined after hybridization in situ, 246 silver grains associated with the chromosomes were counted and 54 amongst these (21.9%) were localized on chromosome 10. The distribution of the grains on this chromosome was not random: 39 out of 54 (72.2% of the latter) were localized on the q25.2–q26 region of the long arm of chromosome 10.

The POP-66/ULIP-4 gene is therefore found to be situated on chromosome 10 in the q25.2–q26 region. The loci of neurodegenerative diseases and of suppressor genes of tumours involved in different types of cancer have been localized in this chromosome region. The locus of a brain disease of early origin (infantile onset spinocerebellar ataxia) was identified in the 10q24-26 region (Varilo et al., 1996; Nikali et al., 1995). The symptoms of this recessive hereditary degenerative disease which is characterized by ataxia, neuropathy and visual atrophy are similar to those observed in patients suffering from paraneoplastic neurological syndromes with circulating anti-CV2 auto-antibodies (Honnorat et al., 1996). On the other hand, 80% of glioblastomas have mutations in this chromosome region and several suppressor loci involved in different types of tumours (prostate, kidney, small-cell lung cancer and endometrial carcinomas) are localized in this chromosome region. These data support the possibility that POP-66/ULIP-4 plays a crucial role in neurodegeneration and tumorigenesis.

In this respect, it is notable that the expression of ULIP-1 is regulated upwards in neuroblastoma cells differentiated by retinoic acid and that ULIP-1 and ULIP-3 are regulated upwards but ULIP-4 is regulated downwards in differentiated PC12 cells in the presence of NGF, suggesting that the stop in cell growth can be linked to expression levels of the ULIP proteins.

EXAMPLE 10

Expression of ULIP Proteins in Transfected HeLa Cells

A—Materials and Methods

A flag (EcoRI-ATGGACTACAAGGACGACGATGA-CAAGG-BamHI) (SEQ ID No. 27) sequence (Kodak) was cloned in the EcoRI site of pSG5 followed by ULIP-1 (EMBEL X87817), base pairs: 309–2023), ULIP-2 (Y10339, base pairs: 23–1741), ULIP-3 (Y09080, base pairs: 269–1991) or ULIP-4 (Y09079, base pairs: 102–1820), respectively. The HeLa cells were cultured in DMEM media (Gibco) to which 10% of foetal calf serum (v/v) was added. The transfections were carried out by calcium phosphate precipitation (Maniatis et al., 1978). The HeLa cells were mixed with 5 μg of Psg5FLAG-ulip-1, 2, 3 and 4 plasmids and 10 μg of pUC18. Twenty-four hours after the transfection, the HeLa cells were fixed with 4% paraformaldehyde and immunolabelled with different human sera (dilution 1/300), visualized by human anti-IgG antibodies conjugated to FITC (Biosys), or anti-flag antibodies (M2, Kodak) (dilution 1/1000), visualized by anti-rabbit antibodies conjugated to Texas red (Vector).

Double immunolabelling was carried out on the HeLa cells transfected with ULIPs using anti-flag and anti-Pep3 antibodies. In the cells transfected by any cDNA, 10 to 20% among them showed immunolabelling with the anti-flag antibodies visualized by the anti-mouse antibodies conjugated to Texas red.

All the transfected cells were doubly labelled by antibodies directed against Pep3 and a peptide common to the four ULIPs is visualized by rabbit anti-IgG antibodies conjugated to fluorescein.

Double immunolabelling was likewise carried out on HeLa cells transfected with ULIPs using anti-flag and anti-CV2 antibodies. The human sera of patients suffering from PNS with circulating anti-CV2 auto-antibodies labelled the cells transfected by ULIP-4, and an anti-CV2 serum likewise labelled the cells transfected by ULIP-3. No labelling of the cells transfected by ULIP-4 was detected in the control sera of patients without cancer or neurological disease, B) Results After transfection of HeLa cells with cDNAs labelled by the flags of ULIP-4, 10 to 20% of the cells were strongly reactive with anti-flag antibodies and anti-Pep3 antibodies which recognize the ULIP-4s of mammals. The transfected cells were not immunolabelled with control serum of 10 neurological patients without PNS nor with rabbit pre-immune serum. On the other hand, the cells transfected with small cDNA of ULIP-4 showed an intense immunoreactivity with all the 7 tested sera of patients with circulating anti-CV2 auto-antibodies. These sera are negative on cells transfected with cDNAs of other ULIPs, with the exception of a sera which also recognized the cells transfected with ULIP-3 and a serum which also recognized the cells transfected with ULIP-1, 3 and 4. No labelling was observed on non-transfected HeLa cells, with an anti-CV2 serum.

Table 1 below shows the results of indirect immunofluorescence with different sera on HeLa cells by labelled cDNAs of members of the ULIP family.

TABLE 1

| Serum No. | Neurological Symptoms | Type of Tumour | ULIP-1 | ULIP-2 | ULIP-3 | ULIP-4 |
|---|---|---|---|---|---|---|
| Anti-Pep3 | — | — | + | + | + | + |
| Pre-immune Pep3 | — | — | − | − | − | − |
| 90-002 | PCD, uveitis | UC | − | − | + | + |
| 93-484 | LE | Thymoma | − | − | − | + |
| 94-590 | LE | SCLC | − | − | − | + |
| 95-700 | PEM | SCLC | + | − | + | + |
| 95-701 | PCD | Uterine sarcoma | − | − | − | + |
| 95-706 | LE, neuropathy | SCLC | − | − | − | + |
| 97-040 | PCD | SCLC | − | − | − | + |
| 97-103 | PCD | SCLC | − | − | − | + |

PCD: paraneoplastic cerebellar degeneration;
LE: limbic encephalitis;
PEM: paraneoplastic encephalomyelitis;
UC: undifferentiated carcinoma;
SCLC: small-cell lung carcinoma.

EXAMPLE 11

Expression of POP-66/ULIP-4 and of Members of the ULIP Family in Cancers

A—Expression of ULIP-2 and ULIP-3 in Cancers:

1) Materials and Methods: RT-PCR Experiments:

The total RNA was extracted using 1 ml of RNAZOL™B (Bioprobe) according to the method of Chomczynski and Sacchi. The quantity of RNA was determined by optical density measured at 260 nm and its purity was determined from the ratio of the absorbances measured at 260 and 280 nm (ratios 1.8–2.0). The integrity of the RNA preparations was additionally checked by electrophoresis on 1% agarose gel in TBE (0.45 M Tris-borate, 10 mM EDTA, pH 8). The specificity of the primers was analysed by comparing their sequences with the various gene databanks (EMBL and FASTA). For a relative quantification, the gene coding for G3PDH (glyceraldehyde-3-phosphate dehydrogenase, Clontech), a ubiquitous gene expressed in numerous tissues including the brain, was co-amplified with the mRNA tested as an internal standard to check the uniformity of the quantities of RNA in the samples and to test the efficacy of the reverse transcription step for different RNA samples. The primers 5', 3' and the oligonucleotides of internal probes of G3PDH were synthesized and purified by Eurogentec. The total mRNA (1 µg) was denatured (15 minutes at 65° C.) and transcribed in single-stranded cDNA (1 and a half hours, 42° C.) in a final volume of 20 µl of buffer (50 mM Tris HCl, 75 mM KCl, pH 8.3, Gibco BRL) containing 5 ng per µl of oligo-dT 12–18 primer (Pharmacia Biotech), 40 units of reverse transcriptase of the Moloney murine leukaemia virus (Mu-LV) (Gibco BRL), 40 units of RNAsine (Promega), 10 mM DTT (Gibco BRL) and 0.5 mM of each of the triphosphate deoxynucleotides (Promega). The cDNA samples were diluted to 1/10 in distilled water and the PCR reactions were carried out using 1 µl, 4 µl or 2 µl of cDNA sample for the messenger RNA of ULIP-2 and ULIP-3, in a buffer (50 mM KCl, 10 mM Tris-HCl, 0.1% Triton X100, 0.4% glycerol and 800 µM NaCl, pH 9), to which was added 40 µmol of DTT, 3 mmol of MgCl$_2$, 0.2 mmol of each dNTP, 0.4 µM of each selected primer and 2 units of AmpliTaq DNA polymerase (Promega) in a final volume of 50 µl). The samples were then placed in a thermocycler (Biomed-Hybaid), denatured at 95° C. for 5 minutes and amplified for 35 cycles (one cycle=95° C. denaturation for 65 seconds, 60° C. hybridization of the primers for 45 seconds, 72° C. extension for 4 minutes and 15 minutes final elongation at 72° C. The products were separated by electrophoresis on 1% Seakem agarose gel and the test bands of the RT-PCR products of expected size as well as the molecular weight marker scale (100 base pairs) (Promega) were visualized using ethidium bromide staining.

Composition of the oligonucleotide probes used for ULIP-3 PCR 5' ATAGAGGAGCGGATGACG (899) (SEQ ID No. 28) 3'

GCTGTTATGGTCTTCAACTTGTCGG (SEQ ID No. 29) (1092)

GGCCTGTTATGGTCTTCMCTTGTCG (SEQ ID No. 30) (1093)

Composition of the oligonucleotide probes used for ULIP-2 PCR 5' AGGAGGAGTGAAGACCATCG (SEQ ID No. 31) (5227) 3'

CTTATGCCACTCGCTGATGTCC (SEQ ID No. 32) (509).

2) Results

The RT-PCR experiments show that TOAD-64 (ULIP-2) and C-22 (ULIP-3) are expressed in certain small-cell lung tumours (cf. FIG. 8) and absent in others, especially in cells of patients who develop paraneoplastic neurological syndromes with a good prognosis.

B—Expression of ULIP-4 in Cancers

1) Materials and Methods

Preparation of the RNA and RT-PCR

The total RNAs are extracted from cerebral tumours preserved in liquid nitrogen according to the conventional RNAZOL™ technique (Bioprobe, France). Reverse transcription was carried out using oligo(dt)$_{18}$ on 1 µg of total RNA and the PCR was carried out with 1/20 of the volume of the mixture for the reverse transcription (RT mix). The primers used for ULIP-4 are: 5'CATCTGGCTGTCGCTG-CAC3' (SEQ ID No. 33), 5'GCCGCCCCTACCA-GAGACC3' (SEQ ID No. 34), and for GAPDH: 5'GGAGATTCAGTGTGGTGG3' (SEQ ID No. 35), 5'GGCTCTCCAGAACATCATCC3' (SEQ ID No. 36). The cDNA was denatured at 95° C. for five minutes. PCR amplification was carried out for 30 cycles. ULIP-4: 95° C., 45 sec; 62° C., 45 sec; 72° C., 45 sec. GAPDH: 95° C., 45 sec; 55° C., 45 sec; 72° C., 45 sec. The final extension was carried out at 72° C. for 5 minutes.

2) Results

Of the 8 glioblastoma extracts studied, 4 (50%) expressed the messenger RNA of ULIP-4. Conversely, of the 10 oligodendroglioma extracts tested, none expressed the messenger RNA of ULIP-4. This differential expression, as a function of the primitive cerebral tumour type, is in favour of a potential role of ULIP-4 in the cell proliferation of these tumours.

The protein POP-66/ULIP-4 as well as the proteins of the ULIP family could be expressed in the peripheral tumours (small-cell lung tumour, thymoma, cancer of the breast and of the ovary). Their presence could therefore be correlated with a prognosis. The localization of the POP-66/ULIP-4 gene on the distal part of chromosome 10 confirms this in the case of cerebral tumours.

Thus, the differential expression of members of the ULIP family in tumours such as small-cell lung cancer, although the corresponding ULIP gene is absent in a healthy tissue, as well as the modulation of the expression of members of the ULIP family obtained during differentiation by the HTLV1 human retrovirus of a medulloblastoma line, suggest the involvement of ULIPs in cancerous tumours.

EXAMPLE 12

Production of Specific Antibodies of each of the Human ULIP Proteins

Specific peptides of each member of the ULIP family were synthesized on a multiple peptide synthesis apparatus using F-moc (432A Peptide Synthesizer SYNERGY, Applied Biosystems). The purity was checked by sequence analysis by HPLC and mass spectrometry.

These peptides are:

Specific peptide of ULIP-1: GSARGSPTRPN (SEQ ID No. 37) (11 amino acids)

Specific peptide of ULIP-2: SSAKTSPAKQQA (SEQ ID No. 38) (12 amino acids)

Specific peptide of ULIP-3: PSAKSSPSKHQ (SEQ ID No. 39) (11 amino acids)

Specific peptide of ULIP-4: PARASCPGKIS (SEQ ID No. 40) (11 amino acids).

1 mg of the synthetic peptide conjugated to limpet haemocyanin, in complete Freund's adjuvant, was used to immunize rabbits with a booster dose of 0.5 mg of bound peptide in complete Freund's adjuvant after 4 weeks.

The antibodies obtained specifically recognize each member protein of the ULIP family.

EXAMPLE 13

Production of Transgenic Animals Expressing ULIP-4

*Drosophila* fruit flies were transformed by the cDNA of human ULIP-4.

The cDNA of ULIP-4, previously cloned in pbluescript SK-phagemid, was excised by Kpn1 and Xba1 enzymatic double digestion, After electrophoresis on agarose gel, the cDNA fragment was purified and then cloned in pUAST, originating from pCaSpeR3, digested by the restriction enzymes Kpn1 and Xba1. The 10-C plasmid results from the directional cloning of the cDNA of ULIP-4 in pUAST associated with the mini-white reporter gene. The 10-C plasmid was injected with a p-delta-2–3 helper plasmid coding for the transposase of the P element active in the germinal line.

The transformed fruit flies are identified by their red eyes resulting from the expression of the mini-white gene. These lines transformed by the cDNA of ULIP-4 under the control of UASGAL4 regulatory sequences allow a targeted expression of the cDNA of ULIP-4.

This production of transformed fruit flies allows the role of ULIP-4 to be studied specifically in different cells and its involvement in human pathologies to be understood.

BIBLIOGRAPHY

Anderson et al., CRC Crit. Rev. Neurobiol., 1987, vol. 3, pp 245–99
Antoine J. C. et al., Journal of the Neurological Sciences, 1993, vol. 117, pp 215–223
Byk et al., Journal of Neuroscience, 1996, vol. 16(2), pp 688–701
Chonczynksky and Sacchi, Anal. Biochem., 1987, 162. 156–159
Dalmau et al., Neurology, 1991, vol. 41, pp 1757–64
Duchemin et al., Dev Neurosci, 1987, vol. 9, pp 61–67
Graus et al., Neurology, 1985, vol. 35, pp 538–543
Graus et al., Neurology, 1990, vol. 40, pp 219–22
Greenlee et al., Ann. Neurol., 1983, vol. 14, pp 609–13
Hamajima et al., Gene, 1996, vol. 180, pp 157–163
Hetzel et al., Mayo Clin. Proc., 1990, vol. 65, pp 1558–63
Honnorat J. et al., Journal of Neurology, Neurosurgery and Psychiatry, 1996, Vol. 61, pp 270–278
Jaeckle et al., Ann. Neurol., 1985, vol. 18, pp 592–600
Köhler and Milstein, Nature, 1975, vol. 256, pp 495–497
Levy N., Mattei M G., 1995, Geneprobs II. A practical approach. B D Hames and S J Higgins, Oxford University Press, pp 211–243
Luque et al., Ann. Neurol., 1991, vol. 29, pp 241–51
Minturn et al., J. Neurosci., 1995, vol. 15, pp 6757–6766
Nikali et al., Am. J. Hum. Genet., 1995, 56, 1088–1095
Peltre G., Lapeyre J.; David B., Immunol. Lett., 1982, vol. 5, pp 127–131
Sambrook et al., Molecular Cloning, a laboratory Manual, 1989, 9.47–9.62
Varilo et al., Genome Res., 1996, 6:870–875
Wang L -H et al., J. Neurosci., 1996, vol. 16(9), pp 6197–6207

The invention claimed is:

1. An isolated nucleic acid, comprising the sequence of SEQ ID No. 7, which encodes a polypeptide comprising the amino acid sequence of SEQ ID NO: 8.

2. A cloning and/or expression vector containing the nucleic acid sequence according to claim 1.

3. An isolated host cell transfected by the vector according to claim 2.

* * * * *